(12) United States Patent
Coulie et al.

(10) Patent No.: US 6,770,456 B1
(45) Date of Patent: Aug. 3, 2004

(54) ENDOGENOUS RETROVIRUS TUMOR ASSOCIATED NUCLEIC ACIDS AND ANTIGENS

(75) Inventors: Pierre Coulie, Brussels (BE); Thierry Boon-Falleur, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/124,398

(22) Filed: Jul. 29, 1998

(51) Int. Cl.[7] .................................................. C12P 21/06
(52) U.S. Cl. ................ 435/69.1; 435/252.3; 435/320.1; 435/325; 536/23.1; 536/24.3; 536/23.5
(58) Field of Search ............................... 536/23.1, 24.3, 536/23.5; 435/325, 69.1, 252.3, 320.1

(56) References Cited

U.S. PATENT DOCUMENTS

| | | | |
|---|---|---|---|
| 4,889,806 A | * 12/1989 | Olson et al. | ............. 435/172.3 |
| 5,342,774 A | 8/1994 | Boon et al. | |
| 5,405,940 A | 4/1995 | Boon et al. | |
| 5,487,974 A | 1/1996 | Boon-Falleur et al. | |
| 5,620,886 A | 4/1997 | Brichard et al. | |
| 5,629,166 A | 5/1997 | van der Bruggen et al. | |

OTHER PUBLICATIONS

GenBank, Accession No: AC003682, 1997.*
Sawbrook et al. (ed). Molecular Cloning, A Lab Manual, 2nd ed., Cold Spring Harbor, pp. 16.3–16.4, and pp. 14.2–14.5, 14.15, 1987.*
Harris et al. J. Amer. Societ. Neplirol. 6: 1125–33, 1995.*
Ahn et al. Nature Genetics 3(4): 283–91, 1993.*
Cawthon et al. Genenics 9(3): 446–60, 1991.*
Yee F et al; Accession No: AF 017337, GenBank and MPSRCH Search report, US 09–124–398–8.R p. 11769, p. 34–36, Aug., 1997.*
Sawbrook et al. Molecular Cloning, A lab. Manual., 2nd ed., Cold Spring Harbor Press, Cold Spring harbor, p. 16.3–16.4, 1989.*
Takeda, J. Accession No: C06260. GenBank. and MPSRCH Search report, p. 15, 1996.*
Alberts Mol. Biol. Cell, 3rd ed, p. 465, 1994.*
Shantz Prite. J. Biochem. Cell Biol 31: 107–122, 1999.*
McClean. Eur. J. Cancer 29A : 2243–2248, 1993.*
Fu EMBO J. 15 : 4392–4401, 1996.*
Sawbrook et al. eds. Mol. Cloning . Cold Spring Harbor Lab. Press, Cold Spring Harbor . p. 10.2–10.3, 1989.*
MPSRCH Search report, p. 15, 2001.*
Traversari et al., *J. Exp. Med.* 176:1453–1457, 1992.
van der Bruggen et al., *Science* 254:1643. 1991.
DePlaen et al., *Immunogenetics* 40:360–369, 1994.
Huang et al., *Proc. Natl. Aces. Sci. USA* 93:9730–9735, 1996.
Löwer et al., *Proc. Natl. Acad. Sci. USA* 93:5177–5184, 1996.
Urnovitz and Murphy, *Clin. Microbiol. Rev.* 9:72–99, 1996.
Medstrand et al., *J. Gen. Virol.* 78:1731–1744, 1997.
Gross, *Proc. Nat'l Acad. Sci. USA* 94:4237–4238, 1997.

* cited by examiner

*Primary Examiner*—Susan Ungar
*Assistant Examiner*—Minh-Tam Davis
(74) *Attorney, Agent, or Firm*—Wolf, Greenfield & Sacks, P.C.

(57) ABSTRACT

The invention describes HERV-AVL3-B tumor associated genes, including fragments and biologically functional variants thereof. Also included are polypeptides and fragments thereof encoded by such genes, and antibodies relating thereto. Methods and products also are provided for diagnosing and treating conditions characterized by expression of a HERV-AVL3-B gene product.

18 Claims, 4 Drawing Sheets

```
                    R                                                                    U5
    ┌─────────────────────────────────────────────────────────────────────────────────┬──────────────────────┐
    │ ctaatgaatacaaagggctgtataagctcagggcccttgttccctagaagcaaggagcccctgacccttctttaaaaca │ gatcttttgtctttgtct   │ 100
    │ tcatttctgcgtttgtccttcttcttcagtcctgaactgacagccaca │ agtggcacctgaacagggacttgaacaaagaaggtctgctggagcagaaaaa   200
    └─────────────────────────────────────────────────┘
                                                       PBS
                                             Splice
    gtgaaactgaccagatgaatgagaaaccctgggatgagtctgcctgcagaggatataag̣agatggataaaccgtgtgagtgccctcaagttgtgtgcga   300
                                             OPC646 ►                                              OPC599
    ccatggaatgggagactggagggatacatggatcccaactacaggcccagctcctccagtatgagccatgagccagttgaatctgaatgtgaagatgaa   400
    tgaagaccgacgagagtcacactgacgtcaaccctcataacatgggtcagatcaagaaaaccacaccagaagctgagaaactggtgtagtgccagggtc   500
    ◄
                     M  L  A  V  I  S  C  A  V  *
    aggcaaaaacccctgactccatgtttatggccatgctagctgtaatatcctgtgcagtatgattttctgtgcagaagcaaaaacatattgggcatattt   600
    tcctaacccaccggtagtgtgatcatactctgaagcagcactcctcctgagatatatcatgatcaaggagcatcagtaccaggacctctaactcccctg   700
    acacagagcaattagactctcataacaatggtatcaattataccactccattggagggacttcctttatgtgtcacccaggatacattgctcaactgcag   800
    ttgccttgcagtttgatcccaagcatggttgagttaccataaaaaaattatgtacctattagacccttagctttattaatattacttgtgtagttactaat   900
    ◄ OPC600
    cactcctggccccatcacccaaattgtactgattatacagaatgggctcccttgataattctcaccccctccttgggcccactgtcttggccccttag   1000
    ctagacaatagtccatgttaatgggagacattattgactgggtcctgtggtcattaagatgggagagatgagaatcagaccacatggcataaacttca   1100
    ctggcactggtggcgaaactttaacatctcttcacttcaacacactgggattcaatcccaatctgccatgcaacttgcttggcatggaacgggctttagc   1200
    ccacctttgcctcaatggcattatcaaggaaagagaggtccaattcaggagtctatgtggaaggcagcactcccatatatgaatggcagcatttgggttg   1300
                                             ◄ OPC601
    ggacactatccaataatagtaatagtgctcaatacagtttaatgttacctttgtaaaaaatgtttgaaatttgtgttttaatccctatgttttctagc   1400
    agcaaaaaggaccaactccaggtaaacaatgcccaattgaattgtgattcctgtcaactctatcattgccttaatcatagcacaatacaaacacacagc   1500
    atatccaccctaataattctaggtcgcattcctggattatggattcctgtaaatctatctgagccttgggcagccaccccacttttacattttgtaaaac   1600
    ttcttactcagcttactcatggcactcgtagagccttaggcatgataattttactatagtctccttaattacattaatacccctcgttgtggtgtcctc   1700
                                                                                              OPC591
    agtagcactggacagctccactcaaacagctcaatatgcagaaaattggatgcatacagctgaccaggcatggatgtttcaaaataaaactaacactgag   1800
    ◄
    atacaaacagaagtggcaatgttaaagactactgttctgtggctagaagaacaagtacaaagcttgcagttgcagtagcaattgcgttgtcattttaacc   1900
    atactcatatttgtgtaaccaattaggaatataatcaaagtgaatatccatggaaccttgtaaaggcccatttacagggagctgttacatccaatgttac   2000
    ttttgatattaatgatttacaaagtaaaattctaacagcacctcaatatcttttcataattattggaataatgttactatgtttctgttttttgttcat   2100
    agtctgtaaaatcaactggaacaccaaccagcaattgagagctgaacagcctgcaattacctttattcaattaaatcaaaagcagaaaggggga │ tgtt   2200
                                                                                              U3
    │ ggaggctgaaagaatgagggtcatgaccaactcagtataccactggaggctatgtgagcaaacagcaaactgttctcatgaatacaggatattggcaagc   2300
    │ tgacagctgcatctgccaccagaaggaatgctgaggacagtcatgcatcaggcacagtgttccttgtagttatctataggaacatctggaccctgttgta   2400
    │ taaagaaagcaatttatttgagcctgtgataaatcaagcagctgactaaaactgttacctcttcctccctgttgattctac │ ctaatacatgtgaagggctg   2500
    │ tataagctcagggcccttgttccctagaagcaaggagcccctgacccttctttacaac │ aaaaaaaaaaaaaaaa   2578
                    R
```

Figure 3

ENDOGENOUS RETROVIRUS TUMOR ASSOCIATED NUCLEIC ACIDS AND ANTIGENS

FIELD OF THE INVENTION

This invention relates to nucleic acid molecules and encoded polypeptides which are expressed preferentially in tumors, particularly in melanomas. The nucleic acid molecules and encoded polypeptides are useful in, inter alia, diagnostic and therapeutic contexts.

BACKGROUND OF THE INVENTION

The phenotypic changes which distinguish a tumor cell from its normal counterpart are often the result of one or more changes to the genome of the cell. The genes which are expressed in tumor cells, but not in normal counterparts, can be termed "tumor associated" genes. These tumor associated genes are markers for the tumor phenotype. The expression of tumor associated genes can also be an essential event in the process of tumorigenesis.

Typically, the host recognizes as foreign the tumor associated genes which are not expressed in normal non-tumorigenic cells. Thus, the expression of tumor associated genes can provoke an immune response against the tumor cells by the host. Tumor associated genes can also be expressed in normal cells within certain tissues without provoking an immune response. In such tissues, expression of the gene and/or presentation of an ordinarily immunologically recognizable fragment of the protein product on the cell surface may not provoke an immune response because the immune system does not "see" the cells inside these immunologically privileged tissues. Examples of immunologically privileged tissues include brain and testis.

The discovery of tumor associated expression of a gene provides a means of identifying a cell as a tumor cell. Diagnostic compounds can be based on the tumor associated gene, and used to determine the presence and location of tumor cells. Further, when the tumor associated gene contributes to an aspect of the tumor phenotype (e.g., unregulated growth or metastasis), the tumor associated gene can be used to provide therapeutics such as antisense nucleic acids which can reduce or substantially eliminate expression of that gene, thereby reducing or substantially eliminating the phenotypic aspect which depends on the expression of the particular tumor associated gene.

As previously noted, the polypeptide products of tumor associated genes can be the targets for host immune surveillance and provoke selection and expansion of one or more clones of cytotoxic T lymphocytes specific for the tumor associated gene product. Examples of this phenomenon include proteins and fragments thereof encoded by the MAGE family of genes, the tyrosinase gene, the Melan-A gene, the BAGE gene, the GAGE gene, the RAGE family of genes, the PRAME gene and the brain glycogen phosphorylase gene, as are detailed below. Thus, tumor associated expression of genes suggests that such genes can encode proteins which will be recognized by the immune system as foreign and thus provide a target for tumor rejection. Such genes encode "tumor rejection antigen precursors", or TRAPs, which may be used to generate therapeutics for enhancement of the immune system response to tumors expressing such genes and proteins.

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, *Science* 257: 880, 1992; Fremont et al., *Science* 257: 919, 1992; Matsumura et al., *Science* 257: 927, 1992; Latron et al., *Science* 257: 964, 1992.

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *J. Exp. Med.* 176:1453–1457, 1992; van der Bruggen et al., *Science* 254: 1643, 1991; De Plaen et al., *Immunogenetics* 40:360–369, 1994 and U.S. Pat. No. 5,342,774 for further information on this family of genes.

In U.S. Pat. No. 5,405,940, the disclosure of which is incorporated by reference, nonapeptides are taught which are presented by the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,629,166, incorporated by reference, the fact that the MAGE-1 expression product is processed to a second TRA is disclosed. This second TRA is presented by HLA-Cw16 molecules, also known as HLA-C*1601. The disclosure shows that a given TRAP can yield a plurality of TRAs.

In U.S. Pat. No. 5,487,974, incorporated by reference herein, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. Pat. No. 5,620,886, incorporated herein by reference in its entirety, a second TRA, not derived from tyrosinase is taught to be presented by HLA-A2 molecules. The TRA is derived from a TRAP, but is coded for by a known MAGE gene. This disclosure shows that a particular HLA molecule may present TRAs derived from different sources.

A recent report by Huang et al. (*Proc. Natl. Acad. Sci. USA* 93:9730–9735, 1996) describes the isolation of a TRA peptide from a chemically induced mouse colon epithelial tumor, CT26. The TRA derived from an endogenous retroviral gene product.

SUMMARY OF THE INVENTION

It now has been discovered that an additional gene, unrelated to any of the foregoing TRAPs, is expressed in a tumor associated pattern in melanoma cells and encodes a TRA. The gene is related to endogenous retrovirus sequences. The invention provides isolated nucleic acid molecules encoding tumor associated polypeptides. The invention also provides expression vectors containing those molecules and host cells transfected with those molecules, as well as isolated polypeptides encoded by the tumor associated nucleic acid molecules (including tumor rejection antigens and fragments of the isolated polypeptides). The foregoing isolated nucleic acid molecules and polypeptides can be used in the diagnosis or treatment of conditions characterized by the expression of a tumor associated gene.

According to one aspect of the invention, an isolated nucleic acid molecule is provided. The molecule hybridizes under stringent conditions to a nucleic acid having a nucleotide sequence as set forth in SEQ ID NO:8. The isolated nucleic acid molecule is a tumor associated polypeptide precursor and codes for a HERV-AVL3-B tumor associated polypeptide. The invention further embraces nucleic acid molecules that differ from the foregoing isolated nucleic acid molecules in codon sequence to the degeneracy of the genetic code. The invention also embraces complements of the foregoing nucleic acids. In certain embodiments, the isolated nucleic acid molecule comprises the nucleic acid sequence of SEQ ID NO:8. In preferred embodiments, the isolated nucleic acid molecule comprises the coding region of the foregoing nucleic acids.

In another aspect of the invention, an isolated nucleic acid molecule comprising the nucleic acid sequence set forth as SEQ ID NO:8 is provided.

According to another aspect of the invention, an isolated nucleic acid molecule is provided which comprises a fragment of nucleotides 1–2560 of SEQ ID NO:8 that is 12 or more nucleotides in length, e.g., between 12 and 2559 nucleotides in length, and complements thereof. In preferred embodiments, the fragment is at least 12, 13, 14, 15, 16, 17, 18, 19, 20, 21, 22, 23, 24, 25, 27, 30, 40 or 50 contiguous nucleotides of the foregoing and every integer therebetween. In another embodiment, the isolated nucleic acid molecule consists of between 12 and 32 contiguous nucleotides of the foregoing. In still another embodiment, the sequence of the unique fragment includes 1, 2, 3, 4, 5, 6, or 7 contiguous nucleotides nonidentical to the sequence claimed in claim 1. Preferred fragments encode immunogenic fragments of the polypeptide encoded by the HERV-AVL3-B nucleic acids.

Methods for identifying HERV-AVL3-B related nucleic acids, including full-length HERV-AVL3-B cDNAs and HERV-AVL3-B genomic DNAs, are also included in the invention. The methods include contacting a nucleic acid sample (such as a cDNA library, genomic library, genomic DNA isolate, etc.) with a nucleic acid probe or primer derived from a HERV-AVL3-B nucleic acid such as SEQ ID NO:8. The nucleic acid sample and the probe or primer hybridizes to complementary nucleotide sequences of nucleic acids in the sample, if any are present, allowing detection of HERV-AVL3-B related nucleic acids. Preferably the probe or primer is detectably labeled. The specific conditions, reagents, and the like can be selected by one of ordinary skill in the art to selectively identify HERV-AVL3-B related nucleic acids.

According to yet another aspect of the invention, the invention involves expression vectors, and host cells transformed or transfected with such expression vectors, comprising the nucleic acid molecules described above. The expression vectors optionally include a nucleic acid molecule which codes for an HLA molecule. Of course, an HLA-encoding nucleic acid molecule can also be contained in a separate expression vector. Host cells transformed or transfected with the foregoing expression vectors are also provided.

According to another aspect of the invention, an isolated HERV-AVL3-B polypeptide is provided which is encoded by a nucleic acid molecule which hybridizes under stringent conditions to a molecule having the nucleic acid sequence of SEQ ID NO:8, nucleic acid molecules which vary from the foregoing according to the degeneracy of the genetic code, and complements of any of the foregoing nucleic acid molecules.

According to yet another aspect of the invention, an isolated polypeptide is provided which comprises a fragment of the foregoing polypeptides. Preferably, the fragment of the isolated polypeptide binds to a polypeptide-binding agent. In other preferred embodiments, the fragment of the isolated polypeptide is an immunogenic peptide, such as a fragment which binds to an antibody or a cytotoxic T lymphocyte. Particularly preferred polypeptides comprise the amino acid sequence set forth in SEQ ID NO:9.

The invention also provides isolated polypeptides which selectively bind a HERV-AVL3-B protein or fragments thereof. Isolated binding polypeptides include antibodies and fragments of antibodies (e.g., Fab, F(ab)$_2$, Fd and antibody fragments which include a CDR3 region which binds selectively to the HERV-AVL3-B proteins of the invention). The isolated binding polypeptides include monoclonal antibodies, humanized antibodies and chimeric antibodies.

In connection with any of the isolated nucleic acids encoding a tumor associated polypeptide as described above, especially a tumor rejection antigen derived from a tumor associated polypeptide, the invention also embraces degenerate nucleic acids that differ from the isolated nucleic acid in codon sequence only due to the degeneracy of the genetic code or complements of any of the foregoing nucleic acids.

According to still another aspect of the invention, methods for diagnosing a disorder characterized by the expression of a tumor associated nucleic acid molecule or a tumor associated polypeptide are provided. The methods involve contacting a biological sample isolated from a subject with an agent that is specific for the tumor associated nucleic acid molecule or an expression product thereof. In certain embodiments, the tumor associated nucleic acid molecule hybridizes under stringent conditions to a molecule having a nucleotide sequence set forth as SEQ ID NO:8. In these certain embodiments, the tumor associated nucleic acid optionally codes for a tumor associated polypeptide. In other embodiments, the agent is a binding agent which selectively binds to a tumor associated polypeptide, such as an antibody, cytotoxic T lymphocyte, polypeptide, and the like. The methods further involve determining the interaction or binding between the agent and the nucleic acid molecule or expression product thereof as a determination of the disorder. In preferred embodiments, the agent is a nucleic acid molecule comprising a molecule having a nucleotide sequence set forth as SEQ ID NO:8, fragments thereof, and complements thereof. In certain embodiments, the interaction between the agent and the nucleic acid molecule is determined by amplifying at least a portion of the nucleic acid molecule. In preferred embodiments, the agent which binds the tumor associated polypeptide is an antibody. In the foregoing embodiments, the biological sample preferably is isolated from a non-testis tissue. In certain of the foregoing embodiments, the tumor associated nucleic acids and polypeptides are fragments of the foregoing sequences.

The recognition that peptides derived from tumor associated polypeptides may be presented by HLA molecules and recognized by CTLs permits diagnosis of certain disorders. Thus, according to another aspect of the invention, a method for diagnosis of a disorder characterized by expression of a tumor rejection antigen derived from a tumor associated polypeptide is provided. The method involves contacting a biological sample isolated from a subject with an agent that is specific for the tumor rejection antigen derived from a tumor associated polypeptide. The method then provides for determining the interaction between the agent and the tumor rejection antigen derived from a tumor associated polypeptide as a determination of the disorder. In certain embodiments, the tumor rejection antigen derived from a tumor associated polypeptide comprises the amino acid sequence of a polypeptide encoded by SEQ ID NO:8 or nucleic acid molecules which hybridize thereto under stringent conditions. In preferred embodiments, the tumor rejection antigen comprises between 7 and 100 consecutive amino acids of the foregoing sequences. Preferably, the biological sample is isolated from non-testis tissue. In certain embodiments, the agent is an antibody.

The above-described method provides diagnosis of a disorder based on the presence of tumor associated TRAs. Another aspect of the invention provides methods for diagnosing a disorder characterized by the expression of a tumor rejection antigen derived from a tumor associated polypeptide which forms a complex with HLA molecules, e.g. the HERV-AVL3-B endogenous retrovirus tumor rejection antigen which forms a complex with HLA-A2 molecules. The method involves contacting a biological sample isolated from a subject with an agent that binds the complex and then determining binding between the complex and the agent as a determination of the disorder. In one embodiment, the tumor rejection antigen derived from a tumor associated polypeptide is a peptide comprising the amino acids of a fragment of a polypeptide encoded by SEQ ID NO:8 or nucleic acid molecules which hybridize thereto under stringent conditions. In certain embodiments, the tumor rejection antigen comprises between 7 and 100 consecutive amino acids of the foregoing sequences, and preferably the tumor rejection antigen is a peptide comprising the amino acids of SEQ ID NO:9. Preferably, the biological sample is isolated from non-testis tissue. In certain embodiments, the agent is an antibody.

In addition to diagnosis of disorders, treatment of certain disorders is also desirable. According to another aspect of the invention, methods for treating a subject with a disorder characterized by expression of a tumor associated nucleic acid or polypeptide is provided. The method involves administering to the subject an agent which reduces the expression of the tumor associated nucleic acid or polypeptide to ameliorate the disorder. The agent is administered in an effective amount. In certain embodiments, the tumor associated nucleic acid or polypeptide is a tumor rejection antigen and the method involves administering to the subject an amount of an agent which enriches selectively in the subject the presence of complexes of HLA and a tumor rejection antigen derived from a tumor associated polypeptide encoded by SEQ ID NO:8 or nucleic acid molecules which hybridize thereto under stringent conditions, sufficient to ameliorate the disorder. Another method involves administering to a subject in need of such treatment an amount of autologous cytolytic T cells sufficient to ameliorate the disorder, wherein the autologous cytolytic T cells are specific for complexes of an HLA molecule and a tumor rejection antigen derived from a tumor associated polypeptide. Preferably the complexes are formed of HLA and the certain tumor associated peptides as described above. In other embodiments, the tumor associated nucleic acid or polypeptide is a nucleic acid and the agent is an antisense nucleic acid. The antisense nucleic acid preferably hybridizes to a tumor associated nucleic acid set forth as SEQ ID NO:8 or nucleic acid molecules which hybridize thereto under stringent conditions and fragments thereof.

According to another aspect of the invention, a composition is provided. The composition comprises an antisense nucleic acid which binds to a tumor associated nucleic acid set forth as SEQ ID NO:8, related HERV-AVL3-B nucleic acids and fragments thereof. The antisense nucleic acid reduces the expression of the tumor associated nucleic acid. The composition also includes a pharmaceutically acceptable carrier.

The invention in another aspect involves a kit for detecting the presence of the expression of a tumor associated polypeptide precursor. Such kits employ two or more of the above-described nucleic acid molecules isolated in separate containers and packaged in a single package. In one such kit, a pair of isolated nucleic acid molecules is provided, each of the pair consisting essentially of a molecule selected from the group consisting of a 12–32 nucleotide contiguous segment of SEQ ID NO:8 and complements thereof, and wherein the contiguous segments are nonoverlapping. Preferably, the pair of isolated nucleic acid molecules is constructed and arranged to selectively amplify at least a portion of an isolated nucleic acid molecule which hybridizes under stringent conditions to a molecule selected from the group consisting of the nucleic acid sequence of SEQ ID NO:8, nucleic acid molecules which differ from the above in codon sequence due to the degeneracy of the genetic code and complements thereof. In certain embodiments, the pair of isolated nucleic acid molecules is PCR primers. Preferably one of the primers is a contiguous segment of SEQ ID NO:8 and another of the primers is a complement of another contiguous segment of SEQ ID NO:8.

According to yet another aspect of the invention, methods for treating a subject with a disorder characterized by expression of a tumor associated nucleic acid as claimed in claim 1 or expression product thereof, e.g. a HERV-AVL3-B endogenous retrovirus tumor rejection antigen, are provided. The methods include administering to the subject an amount of an agent, which enriches selectively in the subject the presence of complexes of an HLA molecule and a polypeptide encoded by the tumor associated nucleic acid as claimed in claim 1, effective to ameliorate the disorder. In certain embodiments the disorder is cancer. Preferably, the HERV-AVL3-B endogenous retrovirus tumor rejection antigen is a peptide which comprises the amino acids set forth in SEQ ID NO:9.

According to another aspect of the invention, methods for treating a subject having a condition characterized by expression of a tumor associated antigen (e.g., a HERV-AVL3-B endogenous retrovirus tumor rejection antigen) encoded by a tumor associated nucleic acid as claimed in claim 1 in cells of the subject are provided. The methods include removing an immunoreactive cell containing sample from the subject, contacting the immunoreactive cell containing sample to a host cell under conditions favoring production of cytolytic T cells against the tumor associated antigen. The cytolytic T cells are introduced to the subject in an amount effective to lyse cells which express the tumor associated antigen, and preferably to ameliorate the condition. Preferably the host cell is transformed or transfected with an expression vector comprising the isolated nucleic acid molecule of claim 1 operably linked to a promoter. In certain embodiments the host cell recombinantly expresses an HLA molecule which binds the tumor associated antigen. In other embodiments the host cell endogenously expresses an HLA molecule which binds the tumor associated antigen. In certain preferred embodiments, the HLA presenting molecule is HLA-A2 and the endogenous retrovirus tumor rejection antigen is a peptide comprising the amino acids set forth in SEQ ID NO:9.

The invention in another aspect also provides pharmaceutical preparations containing the agents and/or cells of the preceding paragraphs. In one embodiment, the preparation contains a pharmaceutically effective amount of HERV-AVL3-B polypeptides encoded by the foregoing nucleic acids, or a fragment thereof, that binds an HLA molecule along with pharmaceutically acceptable diluents, carriers or excipients. In another embodiment, the preparation contains a pharmaceutically effective amount of isolated autologous cytolytic T cells specific for complexes of an HLA molecule and a tumor rejection antigen derived from such HERV-AVL3-B polypeptides. Preferred fragments and TRAs comprise the amino acids of SEQ ID NO:9.

According to another aspect of the invention, the use of isolated HERV-AVL3-B polypeptides or nucleic acids, or fragments thereof, in the manufacture of a medicament is provided. Preferred fragments of the HERV-AVL3-B molecules are described above. The use of antisense nucleic acids which bind to a tumor associated nucleic acid in the manufacture of a medicament is also provided. In certain embodiments, the medicament is an injectable medicament, an oral medicament, or an inhalable medicament.

According to another aspect of the invention, the use of isolated HERV-AVL3-B polypeptides or nucleic acids, or fragments thereof, including antisense nucleic acids, in the manufacture of a medicament for the treatment of cancer is provided.

The invention also embraces functional variants and equivalents of all of the molecules described above, including molecules which have additions, substitutions and/or deletions.

These and other objects of the invention will be described in further detail in connection with the detailed description of the invention.

BRIEF DESCRIPTION OF THE DRAWINGS

FIG. 3 shows the sequence of cDNA clone 104 (SEQ ID NO:8) and of the AVL3-B antigenic peptide. Primers are indicated by horizontal arrows: OPC646 and OPC600 were used for the analysis of the expression of the gene; OPC599, OPC600, OPC601 and OPC591 were used for the localization of the antigenic peptide. The LTR U3, and U5 regions are boxed. PBS: primer binding site for a lysine tRNA. Splice: position of the splicing that deleted the gag and pol coding regions. The amino acid sequence MLAVISCAV is SEQ ID NO:9.

DETAILED DESCRIPTION OF THE INVENTION

Figure 1:
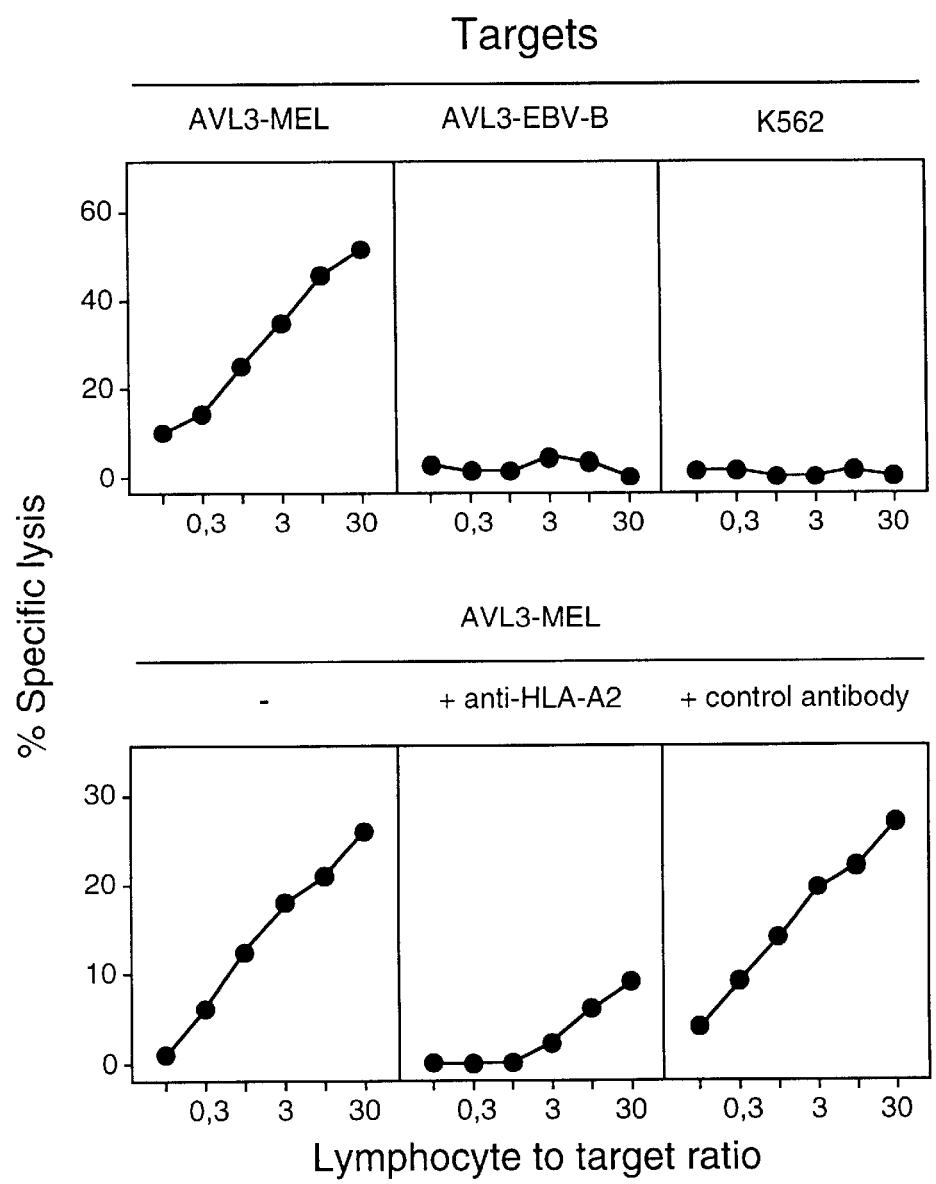
FIG. 1 depicts the sensitivity of $^{51}$Cr-labeled target cells to lysis by anti-AVL3-B CTL clone 13. AVL3-MEL is a melanoma cell line derived from a metastasis resected from patient AVL3. Anti-HLA-A2 monoclonal antibody BB7.2 (IgG2b) was used to inhibit lysis of AVL3-MEL cells by the CTL, by adding a 1:30 dilution of ascitic fluid from mice inoculated with the hybridoma cells. Isotype-matched control antibody was OKMI (anti-CD11b).

The examples which follow show the isolation of nucleic acid molecules which code for polypeptides and are expressed preferentially in tumor cells, i.e. which are tumor associated genes. It is believed that the isolated nucleic acid molecules encode HERV-AVL3-B polypeptides because the nucleic acid molecules were initially isolated from expressed mRNA via RT-PCR amplification. Hence, one aspect of the invention is an isolated nucleic acid molecule which includes all or a fragment of the nucleotide sequence set forth in SEQ ID NO:8. This sequence does not encode a previously recognized tumor rejection antigen precursor, such as a MAGE, BAGE, GAGE, RAGE, LB33/MUM-1, PRAME, NAG, MAGE-Xp, MAGE-B, MAGE-C or brain glycogen phosphorylase sequence, as will be seen by comparing them to the sequence of any of the genes described in the references.

The invention thus involves in one aspect HERV-AVL3-B nucleic acids, encoded polypeptides, functional modifications and variants of the foregoing, useful fragments of the foregoing, as well as therapeutics and diagnostics related thereto.

The invention provides nucleic acid molecules which can code for a HERV-AVL3-B polypeptide and which hybridize under stringent conditions to a nucleic acid molecule consisting of the nucleotide sequence set forth in SEQ ID NO:8. Such nucleic acids are termed tumor associated polypeptide precursors, and may be DNA, RNA, or composed of mixed deoxyribonucleotides and ribonucleotides. The tumor associated polypeptide precursors can also incorporate synthetic non-natural nucleotides.

The invention thus encompasses other tumor associated nucleic acids, some of which may be expressed in normal tissues. A tumor associated nucleic acid or polypeptide is a nucleic acid or polypeptide expressed preferentially in cancer cells, such as tumors including melanoma, etc. Various methods for determining the expression of a nucleic acid and/or a polypeptide in normal and tumor cells are known to those of skill in the art and are described further below. As used herein, tumor associated polypeptides include proteins, protein fragments, and peptides. In particular, tumor associated polypeptides include TRAPs and TRAs.

The term "stringent conditions" as used herein refers to parameters with which the art is familiar. More specifically, stringent conditions, as used herein, refers to hybridization at 65° C. in hybridization buffer (3.5×SSC, 0.02% Ficoll, 0.02% polyvinyl pyrolidone, 0.02% Bovine Serum Albumin, 25 mM NaH$_2$PO$_4$ (pH 7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the support upon which the nucleic acid is transferred is washed, for example, in 2×SSC at room temperature and then at 0.1–0.5×SSC/0.1×SDS at temperatures up to 68° C. For example, the membrane upon which the nucleic acid is transferred can be washed at 2×SSC at room temperature and then at 0.1×SSC/0.1×SDS at 65° C. The foregoing set of hybridization conditions is but one example of stringent hybridization conditions known to one of ordinary skill in the art.

There are other conditions, reagents, and so forth which can be used, which result in stringent hybridization (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). The skilled artisan will be familiar with such conditions, and thus they are not given here. It will be understood, however, that the skilled artisan will be able to manipulate the conditions in a manner to permit the clear identification of homologs and alleles of HERV-AVL3-B nucleic acid molecules of the invention. The skilled artisan also is familiar with the methodology for screening cells, preferably cancer cells, and libraries for expression of such molecules which then are routinely isolated, followed by isolation of the pertinent nucleic acid and sequencing. Thus HERV-AVL3-B nucleic acids including full-length cDNAs and genomic DNAs are provided by the invention.

In general homologs and alleles typically will share at least 40% nucleotide identity and/or at least 50% amino acid identity to the coding region of tumor associated nucleic acids, in some instances will share at least 50% nucleotide identity and/or at least 65% amino acid identity and in s till other instances will share at least 60% nucleotide identity and/or at least 75% amino acid identity. Preferred homologs and alleles share nucleotide and amino acid identities with SEQ ID NO:8 and encoded polypeptides of greater than 80%, more preferably greater than 90%, still more preferably greater than 95% and most preferably greater than 99%. The percent identity can be calculated using various, publicly available software tools developed by NCBI (Bethesda, Md.) that can be obtained through the internet (ftp:/ ncbi.nlm.nih.gov/pub/). Exemplary tools include the BLAST system available at http://www.ncbi.nlm.nih.gov, which uses algorithms developed by Altschul et al. (*Nucleic Acids Res.* 25:3389–3402, 1997). Complements of the foregoing nucleic acids also are embraced by the invention.

Also provided are nucleic acid molecules which include the nucleotide sequence of SEQ ID NO:8 and fragments thereof.

The nucleic acids disclosed herein are useful as probes and amplification primers for determining the expression of HERV-AVL3-B genes according to standard hybridization procedures. The nucleic acids also can be used to express tumor associated polypeptides in vitro or in vivo. The nucleic acids also can be used to prepare fragments of such polypeptides useful for e.g., preparation of antibodies. Many other uses will be apparent to the skilled artisan.

In screening for related nucleic acids, such as nucleic acid molecules related in nucleotide sequence to HERV-AVL3-B, a Southern blot may be performed using the foregoing conditions, together with a radioactive probe (e.g. SEQ ID NO:8). After washing the membrane to which the nucleic acid is finally transferred, the membrane can be placed against x-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:8 or complements thereof. A unique fragment is one that is a 'signature' for the larger nucleic acid. It, for example, is long enough to assure that its precise sequence is not found in molecules within the human genome outside of the HERV-AVL3-B nucleic acids defined herein (and human alleles). Those of ordinary skill in the art may apply no more than routine procedures to determine if a fragment is unique within the human genome. Unique fragments, however, exclude fragments completely composed of the nucleotide sequences of any of the following GenBank accession numbers or other previously published sequences as of the filing date of this application: AC003682, AL021917, AF017337, M14139, AC003005, M14138, D86999, U60269, L19439, Z83843, AF055066, AL022157, Z82211, AC004076, AL022069, AL022154, AC002386, U95626, AC004653, AL023280, AC004790, U95743, U95741, AC002541, AC003973, Z69923, AC004381, AB001523, U91320, Z93016, AC005154, U60270, U73641, X91625, AB000878, U65416, U60268, AB000882, AC004699, Z99496, AC003100, L19399, D89667, AC003044, AC002992, L19398, D86250, AC003072, AC002080, U51998, Z84814, U86698, AJ006287, X66845, AC004321, Z72510, AA905153, AA557252, AA946658, AA860817, AA633377, AA703830, AA994562, W45028, W44596, C06260, AI040849, T91425, W81395, AI027475, AA969810, W39533, W92722, AA719143, W42719, W68352, W79742, AA835750, W16554, AA292296, R63906, AA854823, AA682762, W69830, AA635862, W56876, AA809711, AA988929, W92678, AA399198, AA659630, W37684, W37685, AI015298, AA657360, AA484777, N34889, AA235038, N89672, N89665, T99873, AA045334, R95037, T80900, AA135905, T82959, AA772746, H47223, AA491542, AA362908, AA902358, W16769, H56986, N91490, AA922806, AA225868, W95614, AA446441, AA777175, AA195132, W03459, AA530978, AA746165, AA740425, AA906574, W49699, W95615, AA195278, AA676313, AI039288, N20081, AA308934, AA512907, W69940, AA847321, R65589, AA502159, AA045392, W44615, AA971468, T99775, AA939174, W42807, W47247, AA984513, AF009784, W68444, AA297883, N59820, R28225, AA318253, C16725, W15333, AA398619, N41060, AA594852, AA790515, C87818, AA960266, AA285517, C86531, AA896562, AA624334, AA681765, W83449, W15730, AI020305, AA895354, AA104683, AA990336, AA896016, AI020528, AA060100, AA896033, AA919752, AA210417, AA867305, AA072831, AA920957, AA155017, AA896813, W98386, AI058552, AA605383, C36938, C08480, C55215, C23811, H35646, D24029, AA659958, AA661399, D34402, and C51955.

A fragment which is completely composed of a sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of HERV-AVL3-B polypeptides, useful, for example, in the preparation of antibodies, and in immunoassays. Unique fragments further can be used as antisense molecules to inhibit the expression of HERV-AVL3-B nucleic acids and polypeptides, particularly for therapeutic purposes as described in greater detail below.

As will be recognized by those skilled in the art, the size of the unique fragment will depend upon its conservancy in the genetic code. Thus, some regions of HERV-AVL3-B sequences, such as SEQ ID NO:8, and complements thereof will require longer segments to be unique while others will require only short segments, typically between 12 and 32 nucleotides or more in length (e.g. 12, 13, 14, 15, 16, 17, 18, 19,20, 21, 22, 23, 24, 25, 26, 27, 28, 29, 30, 31 and 32 or more), up to the entire length of the disclosed sequence. The invention embraces each and every fragment of the HERV-AVL3-B sequence, beginning at the first nucleotide, the second nucleotide and so on, up to 8 nucleotides short of nucleotide 2560, and ending anywhere from nucleotide number 8, 9, 10 and so on, up to nucleotide 2560 (provided the sequence is unique as described above).

Virtually any segment of the polypeptide coding region of HERV-AVL3-B nucleic acids, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome. A comparison of the sequence of the fragment to those on known databases typically is all that is necessary, although in vitro confirmatory hybridization and sequencing analysis may be performed.

A unique fragment can be a functional fragment. A functional fragment of a nucleic acid molecule of the invention is a fragment which retains some functional property of the larger nucleic acid molecule, such as coding for a functional polypeptide, binding to proteins, regulating transcription of operably linked nucleic acids, and the like. One of ordinary skill in the art can readily determine using the assays described herein and those well known in the art to determine whether a fragment is a functional fragment of a nucleic acid molecule using no more than routine experimentation.

For any pair of PCR primers constructed and arranged to selectively amplify, for example, a HERV-AVL3-B nucleic acid, a HERV-AVL3-B specific primer may be used. Such a primer is a contiguous stretch of HERV-AVL3-B which hybridizes selectively to HERV-AVL3-B nucleic acids. Such a specific primer would fully hybridize to a contiguous stretch of nucleotides only in HERV-AVL3-B nucleic acids, but would hybridize at most only in part to genes that do not share the nucleotides to which the HERV-AVL3-B specific primer binds. For efficient PCR priming and HERV-AVL3-B nucleic acid identification, the HERV-AVL3-B specific primer should be constructed and arranged so it does not hybridize efficiently at its 3' end to genes other than HERV-AVL3-B. Preferably the area of non-identity is at least one to four nucleotides in length and forms the 3' end of the HERV-AVL3-B specific primer. The kinetics of hybridization then will strongly favor hybridization at the 5' end. In this instance, 3' initiated PCR extension will occur only when both the 5' and 3' ends hybridize to the nucleic acid. Exemplary primers include SEQ ID NO:2 and SEQ ID NO:3, which are derived from SEQ ID NO:8. Other exemplary primers can differ from the above by addition or deletion of 1, 2, 3, 4, 5, or more nucleotides from the 5' end of the primer. One of ordinary skill in the art can determine with no more than routine experimentation the preferred primers for selective amplification of HERV-AVL3-B and related genes. Additional methods which can distinguish nucleotide sequences of substantial homology, such as ligase chain reaction ("LCR") and other methods, will be apparent to skilled artisans.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

The invention also provides isolated polypeptides which include translation products of SEQ ID NO:8, translation products of related HERV-AVL3-B nucleic acids (such as cDNAs including the full-length coding region of HERV-AVL3-B) and fragments thereof. Such polypeptides are useful, for example, alone or as fusion proteins to generate antibodies, as components of an immunoassay, or for determining the binding specificity of HLA molecules and/or CTL clones for HERV-AVL3-B proteins.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other complement proteins.

A fragment of a HERV-AVL3-B protein, for example, generally has the features and characteristics of fragments including unique fragments as discussed above in connection with nucleic acids. As will be recognized by those skilled in the art, the size of a fragment which is unique will depend upon factors such as whether the fragment constitutes a portion of a conserved protein domain. Thus, some regions of HERV-AVL3-B polypeptides will require longer segments to be unique while others will require only short segments, typically between 5 and 12 amino acids (e.g. 5, 6, 7, 8, 9, 10, 11 and 12 amino acids long).

Fragments of a polypeptide preferably are those fragments which retain a distinct functional capability of the polypeptide. Functional capabilities which can be retained in a fragment of a polypeptide include interaction with antibodies, interaction with other polypeptides or fragments thereof, selective binding of nucleic acids, and enzymatic activity. A tumor rejection antigen is an example of a fragment of a tumor associated polypeptide which retains the functional capability of HLA binding and interaction with T lymphocytes. Tumor rejection antigens presented by HLA class I molecules typically are 9 amino acids in length, although peptides of 8, 9 and 10 and more amino acids also retain the capability to interact with HLA and T lymphocytes to an extent effective to provoke a cytotoxic T lymphocyte response (see, e.g., Van den Eynde & Brichard, *Curr. Opin. Immunol.* 7:674–681, 1995; Coulie et al., *Stem Cells* 13:393–403, 1995). Similarly, tumor rejection antigens (e.g., 10–20 amino acids in length) can interact with HLA class II molecules and T helper lymphocytes, provoking proliferation and response of the T helper lymphocytes (see, e.g., Van den Eynde & van der Bruggen, *Curr. Opin. Immunol.* 9:684–693, 1997; Topalian et al., *J. Exp. Med.* 183:1965–1971, 1996).

Those skilled in the art are well versed in methods for selecting unique amino acid sequences, typically on the basis of the ability of the fragment to selectively distinguish the sequence of interest from non-family members. A comparison of the sequence of the fragment to those in known data bases typically is all that is necessary.

The skilled artisan will also realize that conservative amino acid substitutions may be made in HERV-AVL3-B polypeptides to provide functionally active homologs of the foregoing polypeptides, i.e, the homologs retain the functional capabilities of the HERV-AVL3-B polypeptides. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide derived from a HERV-AVL3-B polypeptide is presented by a MHC molecule and recognized by CTLs (e.g., as described in the Examples), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13–18, 1995; Drijfhout et al., *Human Immunol.* 43:1–12, 1995). The substituted peptides can then be tested for binding to the MHC molecule and recognition by CTLs when bound to MHC. These variants can be tested for improved stability and are useful, inter alia, in vaccine compositions.

Functionally equivalent variants of HERV-AVL3-B polypeptides, i.e., variants of polypeptides which retain the function of the natural polypeptides, can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. For example, exemplary functionally equivalent variants of the HERV-AVL3-B polypeptides include conservative amino acid substitutions of polypeptides encoded by SEQ ID NO:8. Conservative amino-acid substitutions in the amino acid sequence of HERV-AVL3-B polypeptides to produce functionally equivalent variants of HERV-AVL3-B polypeptides typically are made by alteration of the nucleic acid encoding a HERV-AVL3-B polypeptide (e.g. SEQ ID NO:8). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a HERV-AVL3-B polypeptide. Where amino acid substitutions are made to a small unique fragment of a HERV-AVL3-B polypeptide, such as a 9 amino acid peptide, the substitutions can be made by directly synthesizing the peptide. The activity of functionally equivalent fragments of HERV-AVL3-B polypeptides can be tested by cloning the gene encoding the altered HERV-AVL3-B polypeptide into a bacterial or mammalian expression vector, introducing the vector into an appropriate host cell, expressing the altered HERV-AVL3-B polypeptide, and testing for a functional capability of the HERV-AVL3-B polypeptides as disclosed herein.

As mentioned above, the invention embraces antisense oligonucleotides that selectively bind to a tumor associated gene nucleic acid molecule, including those encoding a HERV-AVL3-B protein, to decrease transcription and/or translation of tumor associated genes. This is desirable in virtually any medical condition wherein a reduction in tumor associated gene product expression is desirable, including to reduce any aspect of a malignant cell phenotype attributable to tumor associated gene expression, such as expression of HERV-AVL3-B. Antisense molecules, in this manner, can be used to slow down or arrest such aspects of a malignant cell phenotype as found in, inter alia, melanoma.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:8 or upon allelic or homologous genomic and/or DNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 (Wagner et al., Nature Biotechnology 14:840–844, 1996) and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439–457, 1994) and at which proteins are not expected to bind. Finally, although, SEQ ID NO:8 discloses a partial cDNA sequence, one of ordinary skill in the art may easily derive the full length cDNA and/or genomic DNA corresponding to SEQ ID NO:8. Thus, the present invention also provides for antisense oligonucleotides which are complementary to the full length cDNA and/or genomic DNA corresponding to SEQ ID NO:8. Similarly, antisense to allelic or homologous DNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, peptides, and carboxymethyl esters.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Modified oligonucleotides also can include base analogs such as C-5 propyne modified bases (Wagner et al., Nature Biotechnology 14:840–844, 1996). The present invention, thus, contemplates pharmaceutical preparations containing modified antisense molecules that are complementary to and hybridizable with, under physiological conditions, nucleic acids encoding tumor associated proteins, together with pharmaceutically acceptable carriers.

It will also be recognized from the examples that the invention embraces the use of the HERV-AVL3-B sequences in expression vectors, as well as to transfect host cells and cell lines, be these prokaryotic (e.g., E. coli), or eukaryotic (e.g., CHO cells, COS cells, yeast expression systems and recombinant baculovirus expression in insect cells). Especially useful are mammalian cells such as mouse, hamster, pig, goat, primate, etc. They can be of a wide variety of tissue types, including mast cells, fibroblasts, oocytes and lymphocytes, and they may be primary cells or cell lines. Specific examples include dendritic cells, U293 cells, peripheral blood leukocytes, bone marrow stem cells and embryonic stem cells. The expression vectors require that the pertinent sequence, i.e., those nucleic acids described supra, be operably linked to a promoter. Especially preferred are nucleic acids encoding a series of epitopes, known as "polytopes". The epitopes can be arranged in sequential or overlapping fashion (see, e.g., Thomson et al., Proc. Natl. Acad. Sci. USA 92:5845–5849, 1995; Gilbert et al., Nature Biotechnol. 15:1280–1284, 1997), with or without the natural flanking sequences, and can be responses.

Thus, for example, peptides derived from the polypeptide having an amino acid sequence encoded by the nucleic acid of SEQ ID NO:8, and which are presented by MHC molecules and recognized by CTL or T helper lymphocytes can be combined with peptides from other tumor rejection antigens (e.g. by preparation of hybrid nucleic acids or polypeptides) to form "polytopes". Exemplary tumor associated peptide antigens that can be administered to induce or enhance an immune response are derived from tumor associated genes and encoded proteins including MAGE-1, MAGE-2, MAGE-3, MAGE-4, MAGE-5, MAGE-6, MAGE-7, MAGE-8, MAGE-9, MAGE-10, MAGE-11, GAGE-1, GAGE-2, GAGE-3, GAGE-4, GAGE-5, GAGE-6, BAGE-1, RAGE-1, LB33/MUM-1, PRAME, NAG, MAGE-Xp2, MAGE-Xp3, MAGE-Xp4, tyrosinase, brain glycogen phosphorylase, Melan-A, MAGE-C1 and MAGE-C2. For example, antigenic peptides characteristic of tumors include those listed in Table 1 below.

TABLE I

Exemplary Antigens

| Gene | MHC | Peptide | Position | SEQ ID NO: |
|---|---|---|---|---|
| MAGE-1 | HLA-A1 | EADPTGHSY | 161–169 | 10 |
|  | HLA-Cw16 | SAYGEPRKL | 230–238 | 11 |
| MAGE-3 | HLA-A1 | EVDPIGHLY | 168–176 | 12 |
|  | HLA-A2 | FLWGPRALV | 271–279 | 13 |
|  | HLA-B44 | MEVDPIGHLY | 167–176 | 14 |
| BAGE | HLA-Cw16 | AARAVFLAL | 2–10 | 15 |
| GAGE-1,2 | HLA-Cw16 | YRPRPRRY | 9–16 | 16 |
| RAGE | HLA-B7 | SPSSNRIRNT | 11–20 | 17 |
| GnT-V | HLA-A2 | VLPDVFIRC(V) | 2–10/11 | 18,19 |
| MUM-1 | HLA-B44 | EEKLIVVLF | exon 2/intron | 20 |
|  |  | EEKLSVVLF (wild type) |  | 21 |
| CDK4 | HLA-A2 | ACDPHSGHFV | 23–32 | 22 |
|  |  | ARDPHSGHFV (wild type) |  | 23 |
| β-catenin | HLA-A24 | SYLDSGIHF | 29–37 | 24 |
|  |  | SYLDSGIHS (wild type) |  | 25 |
| Tyrosinase | HLA-A2 | MLLAVLYCL | 1–9 | 26 |
|  | HLA-A2 | YMNGTMSQV | 369–377 | 27 |
|  | HLA-A2 | YMDGTMSQV | 369–377 | 43 |
|  | HLA-A24 | AFLPWHRLF | 206–214 | 28 |
|  | HLA-B44 | SEIWRDIDF | 192–200 | 29 |
|  | HLA-B44 | YEIWRDIDF | 192–200 | 30 |
|  | HLA-DR4 | QNILLSNAPLGPQFP | 56–70 | 31 |
|  | HLA-DR4 | DYSYLQDSDPDSFQD | 448–462 | 32 |
| Melan-A$^{MART-1}$ | HLA-A2 | (E)AAGIGILTV | 26/27–35 | 33,34 |
|  | HLA-A2 | ILTVILGVL | 32–40 | 35 |
| gp100$^{Pmel117}$ | HLA-A2 | KTWGQYWQV | 154–162 | 36 |
|  | HLA-A2 | ITDQVPFSV | 209–217 | 37 |
|  | HLA-A2 | YLEPGPVTA | 280–288 | 38 |
|  | HLA-A2 | LLDGTATLRL | 457–466 | 39 |
|  | HLA-A2 | VLYRYGSFSV | 476–485 | 40 |
| PRAME | HLA-A24 | LYVDSLFFL | 301–309 | 41 |
| MAGE-6 | HLA-Cw16 | KISGGPRISYPL | 292–303 | 42 |

The peptides of SEQ ID NOs: 30, 41 and 42 are presented in U.S. application Ser. No. 08/724,774, PCT application publication no. WO96/10577 and U.S. application Ser. No. 08/713,354, respectively. Other exemplary peptides include those listed in U.S. Patent applications Ser. Nos. 08/672,351, 08/669,590, 08/487,135, 08/530,569 and 08/880,693. Other examples will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more HERV-AVL3-B peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13):5845–5849, 1995; Gilbert et al., *Nature Biotechnol.* 15(12):1280–1284, 1997; Thomson et al., *J. Immunol.* 157 (2):822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

In instances in which a human HLA class I molecule presents tumor rejection antigens derived from HERV-AVL3-B nucleic acids, the expression vector may also include a nucleic acid sequence coding for the HLA molecule that presents any particular tumor rejection antigen derived from these nucleic acids and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for the tumor rejection antigen precursor and the HLA molecule which presents it are contained on separate expression vectors, the expression vectors can be cotransfected. The tumor rejection antigen precursor coding sequence may be used alone, when, e.g. the host cell already expresses a HLA molecule which presents a TRA derived from HERV-AVL3-B TRAPs. Of course, there is no limit on the particular host cell which can be used. As the vectors which contain the two coding sequences may be used in any antigen-presenting cells if desired, and the gene for tumor rejection antigen precursor can be used in host cells which do not express a HLA molecule which presents a HERV-AVL3-B TRA. Further, cell-free transcription systems may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g. β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with the initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences, 5' or 3'. The choice and design of an appropriate vector is within the ability and discretion of one of ordinary skill in the art.

Expression vectors containing all the necessary elements for expression are commercially available and known to those skilled in the art. See *Molecular Cloning: A Laboratory Manual*, J. Sambrook, et al., eds., Second Edition, Cold Spring Harbor Laboratory Press, Cold Spring Harbor, N.Y., 1989. Cells are genetically engineered by the introduction into the cells of heterologous DNA (RNA) encoding the HERV-AVL3-B tumor associated polypeptide or fragment or variant thereof. The heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer*, 67:303–310, 1996). Also included are bacterial systems for delivery of antigens to eukaryotic cells, such as those which utilize Yersinia (e.g. Starnbach and Bevan, *J. Immunol.* 153:1603, 1994) and Listeria (Dietrich et al., *Nature Biotechnol.* 16:181, 1998). Still other delivery and expression systems will be known to one of ordinary skill in the art.

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also involves agents which bind to tumor associated polypeptides encoded by HERV-AVL3-B nucleic acid molecules ("HERV-AVL3-B polypeptides"), and in certain embodiments preferably to unique fragments of the HERV-AVL3-B polypeptides. Such binding partners can be used in screening assays to detect the presence or absence of a HERV-AVL3-B polypeptide and in purification protocols to isolate HERV-AVL3-B polypeptides. Likewise, such binding partners can be used to selectively target drugs, toxins or other molecules to leukemia cells which present HERV-AVL3-B tumor associated polypeptides. In this manner, cells present in solid or non-solid tumors which express HERV-AVL3-B tumor associated polypeptides can be treated with cytotoxic compounds.

The invention, therefore, involves antibodies or fragments of antibodies having the ability to selectively bind to HERV-AVL3-B tumor associated polypeptides, and preferably to unique fragments thereof. Antibodies include polyclonal and monoclonal antibodies, prepared according to conventional methodology.

The antibodies of the present invention thus are prepared by any of a variety of methods, including administering protein, fragments of protein, cells expressing the protein or fragments thereof and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the TRA/HLA complexes described herein.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR1) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies. Thus, the invention involves polypeptides of numerous size and type that bind specifically to tumor associated polypeptides including HERV-AVL3-B polypeptides. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent a completely degenerate or biased array. One then can select phage-bearing inserts which bind to a HERV-AVL3-B tumor associated polypeptide. This process can be repeated through several cycles of reselection of phage that bind to a HERV-AVL3-B polypeptide. Repeated rounds lead to enrichment of phage bearing particular sequences. DNA sequence analysis can be conducted to identify the sequences of the expressed polypeptides. The minimal linear portion of the sequence that binds to the HERV-AVL3-B polypeptide can be determined. One can repeat the procedure using a biased library containing inserts containing part or all of the minimal linear portion plus one or more additional degenerate residues upstream or downstream thereof. Thus, the tumor associated polypeptides of the invention can be used to screen peptide libraries, including phage display libraries, to identify and select peptide binding partners of the tumor associated polypeptides of the invention. Such molecules can be used, as described, for screening assays, for diagnostic assays, for purification protocols or for targeting drugs, toxins and/or labeling agents (e.g. radioisotopes, fluorescent molecules, etc.) to cells which express tumor associated genes such as those leukemia cells which present HERV-AVL3-B polypeptides on the cell surface. Such binding agent molecules can also be prepared to bind complexes of an HERV-AVL3-B polypeptide and an HLA molecule by selecting the binding agent using such complexes. Drug molecules that would disable or destroy tumor cells which express such complexes or HERV-AVL3-B polypeptides are known to those skilled in the art and are commercially available. For example, the immunotoxin art provides examples of toxins which are effective when delivered to a cell by an antibody or fragment thereof. Examples of toxins include ribosome-damaging toxins derived from plants or bacterial such as ricin, abrin, saporin, Pseudomonas endotoxin, diphtheria toxin, A chain toxins, blocked ricin, etc.

The skilled artisan can determine which HLA molecule binds to tumor rejection antigens derived from HERV-AVL3-B tumor rejection antigen precursors by, e.g., experiments utilizing antibodies to block specifically individual HLA class I molecules. For example, antibodies which bind selectively to HLA-A2 will prevent efficient presentation of TRAs specifically presented by HLA-A2. Thus, because the AVL3-B TRA derived from the HERV-AVL3-B tumor associated gene is presented by HLA-A2, the inclusion of anti-HLA-A2 antibodies in an in vitro assay will block the presentation of these TRAs. The HLA specificity of other TRAs can be detemined by like methodology. An assay for determining the nature of the HLA molecule is found in U.S. patent application Ser. No. 08/530,569. Briefly, in determining the HLA molecule type, inhibition experiments were carried out where the production of tumor necrosis factor (TNF) by cytotoxic T lymphocyte (CTL) clone 263/17 was tested in the presence of monoclonal antibodies directed against HLA molecules or against CD4/CD8 accessory molecules. Four monoclonal antibodies were found to inhibit the production of TNF by CTL 263/17: monoclonal antibody W6/32, which is directed against all HLA class I molecules (Parham et al., *J. Immunol.* 123:342, 1979), antibody B1.23.2 which recognizes HLA-B and C molecules (Rebai et al., *Tissue Antigens* 22:107, 1983), antibody ME-1 which specifically recognizes HLA-B7 (Ellis et al., *Hum. Immunol.* 5:49, 1982) and antibody B9.4.1 against CD8. No inhibition was found with antibodies directed against HLA Class II DR molecules (L243: Lampson et al., *J. Immunol.* 125:293 , 1980), against HLA-A3 (GAPA 3: Berger et al., *Hybridoma* 1:87, 1982) or against CD4 (13B.8.82). The conclusion was that CTL 263/17 was of the CD8 type, and recognized an antigen presented by HLA-B7. Similar experiments using widely available anti-HLA antibodies can be performed to determine the nature of a HLA molecule.

The invention as described herein has a number of uses, some of which are described is above. First, the invention permits the artisan to diagnose a disorder characterized by expression of the TRAP. These methods involve determining expression of the TRAP gene, and/or TRAs derived therefrom, such as a TRA presented by HLA-A2, HLA-A26, HLA-B7, etc. In the former situation, such determinations can be carried out via any standard nucleic acid determination assay, including the polymerase chain reaction, or assaying with labeled hybridization probes. In the latter situation, assaying with binding partners for complexes of TRA and HLA, such as antibodies, is especially preferred. An alternate method for determination is a TNF release assay, of the type described supra.

The isolation of the TRAP gene also makes it possible to isolate the TRAP molecule itself, especially TRAP molecules containing the amino acid sequences coded for by SEQ ID NO:8 and related molecules. Other TRAPs or TRAs encoded by tumor associated genes and recognized by other CTL clones and/or presented by other HLA molecules may be isolated by the procedures detailed herein. (There are numerous HLA molecules known to those skilled in the art, including but not limited to, those encoded by HLA-A, HLA-B, HLA-C, HLA-E, HLA-F and HLA-G genes.) A variety of methodologies well-known to the skilled practitioner can be utilized to obtain isolated TRAP molecules. The protein may be purified from cells which naturally produce the protein. Alternatively, an expression vector may be introduced into cells to cause production of the protein. In another method, mRNA transcripts may be microinjected or otherwise introduced into cells to cause production of the encoded protein. Translation of mRNA in cell-free extracts such as the reticulocyte lysate system also may be used to produce protein. Peptides comprising TRAs of the invention may also be synthesized in vitro. Those skilled in the art also can readily follow known methods for isolating proteins in order to obtain isolated TRAPs and/or TRAs derived therefrom. These include, but are not limited to, immunochromotography, HPLC, size-exclusion chromatography, ion-exchange chromatography and immune-affinity chromatography.

These isolated molecules when processed and presented as the TRA, or as complexes of TRA and HLA, such as HLA-A2, HLA-A26 or HLA-B7, etc. may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provoke a CTL response, or be cells which already express both molecules without the need for transfection. Vaccines also encompass naked DNA or RNA, encoding a tumor associated TRA or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993). When "disorder" is used herein, it refers to any pathological condition where the tumor rejection antigen precursor is expressed. An example of such a disorder is cancer, melanomas in particular.

Therapeutic approaches based upon the disclosure are premised on a response by a subject's immune system, leading to lysis of TRA presenting cells, such as HLA-B7 cells. One such approach is the administration of autologous CTLs specific to the complex to a subject with abnormal cells of the phenotype at issue. It is within the skill of the artisan to develop such CTLs in vitro. Generally, a sample of cells taken from a subject, such as blood cells, are contacted with a cell presenting the complex and capable of provoking CTLs to proliferate. The target cell can be a transfectant, such as a COS cell of the type described supra. These transfectants present the desired complex of their surface and, when combined with a CTL of interest, stimulate its proliferation. COS cells, such as those used herein are widely available, as are other suitable host cells. Specific production of a CTL is well known to one of ordinary skill in the art. The clonally expanded autologous CTLs then are administered to the subject. Other CTLs specific to HERV-AVL3-B may be isolated and administered by similar methods.

Another method for selecting antigen-specific CTL clones has recently been described (Altman et al., *Science* 274:94–96, 1996; Dunbar et al., *Curr. Biol.* 8:413–416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The above technology can also be used to monitor CTL generation after administration of a test vaccine.

To detail a therapeutic methodology, referred to as adoptive transfer (Greenberg, *J. Immunol.* 136(5): 1917, 1986; Riddel et al., *Science* 257: 238, 1992; Lynch et al, *Eur. J. Immunol.* 21: 1403–1410, 1991; Kast et al., *Cell* 59: 603–614, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a tumor associated gene sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a tumor associated gene derived TRA is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex. Chen et al., *Proc. Natl. Acad. Sci. USA* 88: 110–114 (1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. For example, nucleic acids which encode a HERV-AVL3-B TRA such as AVL3-B (SEQ ID NO:9) may be operably linked to promoter and enhancer sequences which direct expression of the HERV-AVL3-B TRA in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding HERV-AVL3-B TRAs. Nucleic acids encoding a HERV-AVL3-B TRA also may be inserted into a retroviral genome, thereby facilitating integration of the nucleic acid into the genome of the target tissue or cell type. In these systems, the gene of interest is carried by a microorganism, e.g., a Vaccinia virus, retrovirus or the bacteria BCG, and the materials defacto "infect" host cells. The cells which result present the complex of interest, and are recognized by autologous CTLs, which then proliferate.

A similar effect can be achieved by combining a TRAP or a stimulatory fragment thereof with an adjuvant to facilitate incorporation into HLA presenting cells in vivo. The TRAP is processed to yield the peptide partner of the HLA molecule while the TRA is presented without the need for further processing. Generally, subjects can receive an intradermal injection of an effective amount of a HERV-AVL3-B encoded TRAP, and/or TRAs derived therefrom. TRAs from HERV-AVL3-B also can be combined with TRAs from other tumor associated polypeptides in a polytope arrangement as described above. Initial doses can be followed by booster doses, following immunization protocols standard in the art.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, DQS21, described in PCT application WO96/33739 (SmithKline Beecham), vitamin E and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (*Science* 268: 1432–1434, 1995), GM-CSF and IL-18.

There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284–6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). Tumor cell transfection with B7 has been discussed in relation to in vitro CTL expansion for adoptive transfer immunotherapy by Wang et al. (*J. Immunol.* 19:1–8, 1986). Other delivery mechanisms for the B7 molecule would include nucleic acid (naked DNA) immunization (Kim et al., *Nature Biotechnol.* 15:7:641–646, 1997) and recombinant viruses such as adeno and pox (Wendtner et al., *Gene Ther.* 4:726–735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered.

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637–642, 1997; Fenton et al., *J. Immunother.*, 21:95–108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). In these situations Th help and B7 costimulation signals are not provided. This mechanism might be used in the context of antigen pulsed DC based therapies or in situations where Th epitopes have not been defined within known tumor associated antigen precursors.

A tumor associated antigen polypeptide, or a fragment thereof, also can be used to isolate their native binding partners. Isolation of such binding partners may be performed according to well-known methods. For example, isolated tumor associated antigen polypeptides can be attached to a substrate (e.g., chromatographic media, such as polystyrene beads, or a filter), and then a solution suspected of containing the binding partner may be applied to the substrate. If a binding partner which can interact with tumor associated antigen polypeptides is present in the solution, then it will bind to the substrate-bound tumor associated antigen polypeptide. The binding partner then may be isolated.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus also is contemplated according to the invention.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of stimulating an immune response, the desired response is an increase in antibodies or T lymphocytes which are specific for the immunogen(s) employed. These responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

According to another aspect of the invention, methods for diagnosing a disorder that is characterized by expression of a tumor associated nucleic acid or polypeptide are provided. The methods involve contacting a biological sample isolated from a subject with an agent specific for the tumor associated nucleic acid or polypeptide to detect the presence of the tumor associated nucleic acid or polypeptide in the biological sample. As used herein, "contacting" means placing the biological sample in sufficient proximity to the agent and under the appropriate conditions of, e.g., concentration, temperature, time, ionic strength, to allow the specific interaction between the agent and tumor associated nucleic acid or polypeptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The biological sample can be located in vivo or in vitro. For example, the biological sample can be a tissue in vivo and the agent specific for the tumor associated nucleic acid or polypeptide can be used to detect the presence of such molecules in the hematopoietic tissue (e.g., for imaging portions of the tissue that express the tumor associated gene products). Alternatively, the biological sample can be located in vitro (e.g., a blood sample, tumor biopsy, tissue extract). In a particularly preferred embodiment, the biological sample can be a cell-containing sample, more preferably a sample containing tumor cells.

EXAMPLES

Materials and Methods

Derivation and Culture of CTL 13

Blood mononuclear cells ($3 \times 10^6$ cells) collected from patient AVL3 were stimulated with $4 \times 10^4$ irradiated (100 Gray) AVL3-MEL cells in 2 ml (one well) Iscove's medium (Gibco Laboratories, Grand Island, N.Y.) supplemented with 10% human serum (HS; a pool of decomplemented serum from ABO blood donors), L-arginine (116 mg/L), L-asparagine (36 mg/L), L-glutamine (216 mg/L) and 2-mercaptoethanol ($5 \times 10^{-5}$M) (AAGM). Iscove's+HS+AAGM is referred to as complete medium. On day 2, recombinant human interleukin-6 (rhIL-6; 1000 U/ml, one U/ml gives 50% maximal proliferation of 7TD1 cells (Van Snick et al., Proc. Natl. Acad. Sci. USA 83:9679–9683, 1986)) and recombinant human interleukin-2 (rhIL-12; 5 ng/ml) were added to the culture. On day 8, the responding lymphocytes were restimulated (2 wells) with irradiated AVL3-MEL cells that had been incubated for 2 days in medium containing recombinant human interferon-γ (rhIFN-γ; 50 U/ml; Boehringer-Mannheim, Mannheim, Germany), in complete medium supplemented with recombinant human interleukin-2 (rhIL-2; 5 U/ml, one U/ml gives 50% maximal proliferation of CTLL-2 cells), IL-6 (500 U/ml) and IL-12 (5 ng/ml). On day 10 the concentration of IL-2 was raised to 25 U/ml. On day 14, the lymphocytes were restimulated in two wells as before, but with IL-2 (25 U/ml) only. On day 23 the lymphocytes were cloned by limiting dilution in microwells containing irradiated IFN-γ-treated AVL3-MEL cells (5000/well) and irradiated LG2-EBV cells (approximately $10^5$/well). Medium was complete medium with IL-2 (50 U/ml). The microcultures were restimulated on day 30 and 37 by the addition of irradiated tumor cells and feeder cells in medium with IL-2, as above. Several CTL clones were obtained. One of them was named AVL3-CTL-413/13, hereafter referred to as CTL 13. CTL 13 was later restimulated by mixing in 2 ml wells approximately $3 \times 10^5$ CTL with $10^5$ irradiated IFN-γ-treated AVL3-MEL cells and $10^6$ irradiated LG2-EBV cells in complete medium containing 50 U/ml IL-2.

Lysis by CTL

Sensitivity of target cells to lysis by the CTL was evaluated by a standard $^{51}$Cr-release assay over 4 hr. Some lysis assays were performed in the presence of the following murine monoclonal antibodies: BB7.2, an IgG2b anti-HLA-A2 (from the ATCC), and OKM1, an IgG2b anti-CD11b (from the ATCC).

Construction and Screening of the cDNA Library

Total RNA was extracted from AVL3-MEL cells by the guanidine-isothiocyanate procedure (Davis et al., 1986). Poly(A)+RNA enriched by an oligo(dT)-cellulose column (Pharmacia Biotech) was converted to cDNA with the Superscript Choice System (Gibco BRL) using an oligo(dT) primer 5'-ATAAGAATGCGGCCGCTAAACTA(T)$_{18}$VN (V=G, A or C; N=G, A, T or C) (SEQ ID NO:1) which contains a NotI site at its 5' end. The degenerate 3' end of the oligonucleotide favors annealing at the 5' end of the poly(A) tail of the mRNA molecules, and therefore diminishes the proportion of cDNA clones containing long poly(A) stretches which are difficult to sequence. The cDNA was ligated to HindIII-EcoRI adaptors (Stratagene, La Jolla, Calif.) phosphorylated, digested with NotI, and ligated to plasmid pCEP4 (InVitrogen, Carlsbad, Calif.) digested with HindIII and NotI, and dephosphorylated. Recombinant plasmids were electroporated into E. coli DH5α and selected with ampicillin (50 μg/ml). The library was divided into pools of approximately 100 cDNA clones. Each pool of bacteria was amplified and plasmid DNA was extracted using the QIAprep8 plasmid kit (Qiagen GmbH, Hilden, Germany).

293-EBNA cells (InVitrogen) were transfected with the LipofectAMINE reagent (Gibco-BRL, Gaithersburg, Md.). Briefly, $5-7 \times 10^4$ cells seeded in flat-bottomed microwells were transfected with a mixture consisting of approximately 100 ng of plasmid DNA from a pool of the cDNA library, 50 ng of expression vector pcDNA1/Amp (InVitrogen) containing a genomic HLA-A*0201 sequence, and 1.5 μl of LipofectAMINE. All transfections were performed in duplicate. After 24 h, CTL 13 (3000 cells/well) was added. A further 24 h later, half of the medium was collected and its TNF content measured by testing the cytotoxic effect on WEHI-164c13 cells (Espevik and Nissen-Meyer, *J. Immunol. Methods*, 95:99–105, 1986) in an MTT colorimetric assay (Hansen et al., *J. Immunol Methods*, 119:203–210, 1989).

Localization of the Antigenic Peptide

Four fragments of cDNA were amplified by PCR, using forward primer OPC598 (5'-GTACCAGCTGCTAGCAAG-3', located in plasmid pCEP4 immediately upstream of the cloned cDNA; SEQ ID NO:2), and reverse primers OPC599 (5'-TCGTCGGTCTTCATTCCA-3', corresponding to nt 396–413 of cDNA clone 104; SEQ ID NO:3),OPC600 (5'-GGATCAAACTGCAAGGCA-3', corresponding to nt 802–819 of cDNA clone 104; SEQ ID NO:4), OPC601 (5'-CTTCCACATAGACTCCTG-3', corresponding to nt 1246–1263 of cDNA clone 104; SEQ ID NO:5), or OPC591 (5'-AGTGCTACTGAGGACACC-3', corresponding to nt 1692–1709 of cDNA clone 104; SEQ ID NO:6). PCR conditions were 5 min. at 94° C., followed by 30 cycles (33 cycles with OPC601) consisting of 1 min at 94° C., 2 min at 60° C. (55° C. with OPC601) and 3 min at 72° C., and a final elongation step of 15 min at 72° C. The amplified products were purified by passage through a Chroma Spin 100 column (Clontech, Palo Alto, Calif.), and cloned into expression plasmid pCR3 using the Eukaryotic TA Cloning Kit (InVitrogen). The recombinant plasmids were analysed by PCR to determine the orientation of the inserted cDNA fragment. The relevant constructs were cotransfected, using LipofectAMINE as above, into 293-EBNA cells with the HLA-A2 cDNA clone.

PCR Assay for Expression of the Gene Encoding AVL3-B

Total RNA extraction and reverse transcription of RNA were performed as described previously (Van den Eynde et al., *J. Exp. Med.* 182:689–698, 1995). PCR amplification was performed with DNA polymerase TaKaRa Taq (Takara Biomedicals, Shiga, Japan) using forward primer OPC646 (5'-TGCAGAGGATATAAGGAGAT-3', corresponding to nt 245–264 of cDNA clone 104; SEQ ID NO:7) and reverse primer OPC600.

The following reagents were mixed:

| | |
|---|---|
| H$_2$O | 15.75 µl |
| PCR buffer (10x, TaKaRa) | 2.5 µl |
| dNTP (10 mM each) | 2 µl |
| OPC646 (20 µM) | 1 µl |
| OPC600 (20 µM) | 1 µl |
| TaKaRa Taq | 0.25 µl |
| cDNA (corresponding to 50 ng of total RNA) | 2.5 µl |

PCR conditions were 5 min at 94° C., followed by 29 cycles consisting of 1 min at 94° C., 2 min at 63° C. and 3 min at 72° C., and at a final elongation step of 1.5 min at 72° C. It was verified that these conditions were in the linear range of DNA amplification. The quantities of the amplified DNA were visually assessed with agarose gels stained with ethidium bromide. They were compared with the products of PCR amplification of serial dilutions (1:1, 1:3, 1:9, 1:27) of cDNA from AVL3-MEL cells.

Example 1

A CTL Clone Recognizing AVL3-MEL Cells

Blood mononuclear cells collected from melanoma patient AVL3 were stimuated in vitro with irradiated AVL3-MEL cells, a cell line derived from a metastasis resected from the patient. The responder lymphocytes, restimulated each week by the addition of tumor cells and IL-2, were cloned by limiting dilution. CTL clone 13 was obtained that lysed the autologous AVL3-MEL cells, but did not lyse autologous Epstein-Barr virus (EBV)-transformed B cells (AVL3-EBV) or natural killer target cells K562 (FIG. 1). The antigen recognized by CTL 13 was named AVL3-B. An anti-HLA-A2 monoclonal antibody inhibited recognition of AVL3-MEL cells by CTL 13, indicating that antigen AVL3-B was presented by HLA-A2 molecules.

Example 2

Identification of cDNA Coding for Antigen AVL3-B

Figure 2:
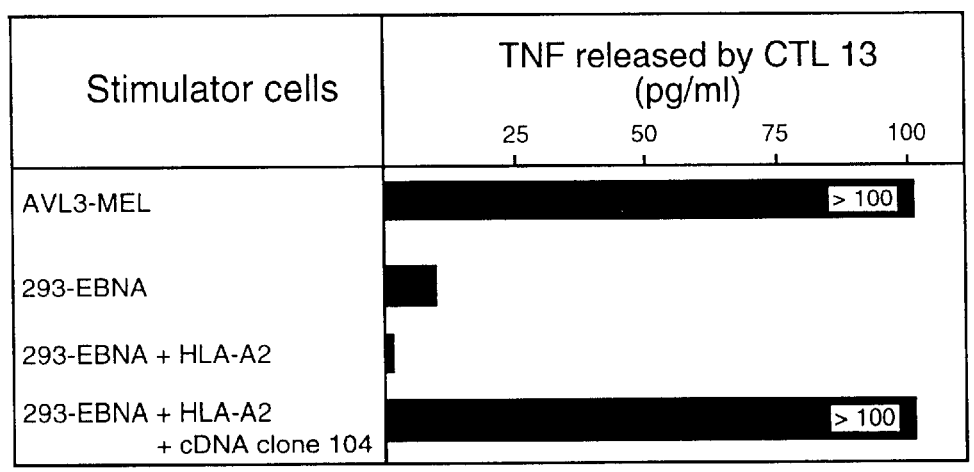
FIG. 2 shows the identification of a cDNA clone encoding antigen AVL3-B. CTL13 was stimulated by 293-EBNA cells cotransfected with vector pCEP4 containing cDNA clone 104 and vector pcDNA1/Amp containing an HLA-A*0201 sequence. Control stimulator cells included the AVL3-MEL cells and 293-EBNA cells transfected with HLA-A2 or cDNA clone 104 alone. The concentration of the TNF released in the medium was measured using the TNF-sensitive WEHI-164c13 cells.

To identify the antigen recognized by CTL 13, a directional cDNA library was prepared with poly(A)$^+$RNA extracted from AVL3-MEL cells. The library was cloned into expression plasmid pCEP4. This vector contains the EBV origin of replication oriP and allows episomal replication of the plasmid when transfected into mammalian cells (Yates et al. *Nature* 313:812–815, 1985). The library was divided into 500 pools of approximately 100 recombinant clones, and DNA was prepared from each pool. Human embryonic kidney cells 293, stably transfected with an EBNA-1 construct (293-EBNA), were contransfected with DNA from each pool and with an HLA-A2 construct. The CTL clone 13 was added to the transfectants after 24 h, and after another 24 h the supernatant was collected and its TNF content was measured with the TNF-sensitive WEHI-164c13 cells. Four pools of cDNA proved positive. One of them was subcloned, and cDNA clone 104 was found to transfer the expression of antigen AVL3-B into 293-EBNA cells (FIG. 2).

Example 3

Characterization of cDNA Clone 104

Clone 104 was sequenced according to standard procedures. The sequence of cDNA 104 was 2578 bp long (SEQ ID NO:8). It did not correspond to sequences present in data banks, but showed homologies with Human Endogenous Retroviruses (HERV) (Löwer et al., *Proc. Natl. Acad. Sci. USA* 93:5177–5184, 1996; Urnovitz and Murphy, *Clin. Microbiol. Rev.* 9:72–99, 1996).

The highest homology (approximately 90% identity) was found with an HERV sequence mapped on chromosome 19 (GenBank accession number AC003682). As shown in FIG. 3, the sequence of cDNA 104 contained the U3, R and U5 regions of retroviral Long Terminal Repeats (LTR), and a primer binding site for the lysine (K) tRNA (UUU), indicating that the sequence belongs to the HERV-K family (Medstrand et al., *J. Gen. Virol.* 78:1731–1744, 1997). Between the 3' and 5' LTRs, the sequence shows homologies with the env gene, but is disrupted by many mutations and does not code for an env protein.

Example 4

Identification of the Antigenic Peptide Recognized by CTL Clone 13

To localize the region encloding the antigenic peptide, fragments of cDNA 104 were amplified by PCR and cloned into an expression plasmid. The constructs were cotransfected into 293-EBNA cells with an HLA-A2 cDNA clone, and the expression of antigen AVL3-B by the transfectants was analysed by adding CTL 13 and measuring the production of TNF by the CTL. The results indicated that the peptide-coding region corresponded to nucleotides 413–819 of cDNA 104.

Figure 4:
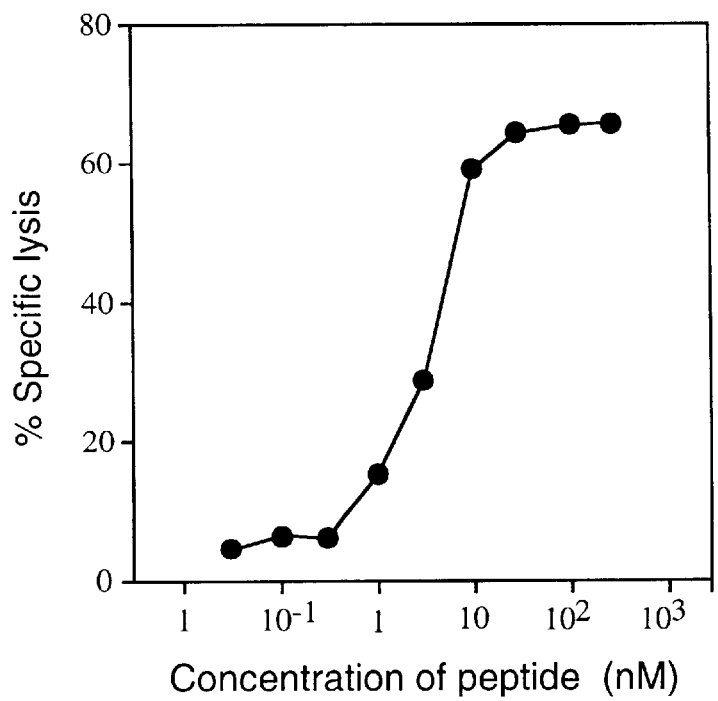
FIG. 4 shows the lysis by CTL 13 of autologous EBV-transformed B cells incubated with peptide MLAVISCAV (SEQ ID NO:9).

Surprisingly, this region, which showed homologies with the env-coding sequences of HERV, did not contain a large open reading frame. The sequence was searched, using the HLA peptide motif search program of the Bioinformatics and Molecular Analysis Section of the NIH (URL http://bimas.dcrt.nih.gov/molbio/hla_bind/index.html), for a peptide predicted to bind to HLA-A2 molecules (Parker et al., *J. Immunol.* 149:3580–3587, 1992). Several peptide sequences were predicted to bind. One of them, MLAVISCAV (SEQ ID NO:9), was contained within an open reading frame starting with an initiation codon preceeded by a canonical Kozak consensus sequence. This peptide sensitized AVL3-EBV B cells to lysis by CTL clone 13, with an half-maximal effect at 5 nM (FIG. 4). $^{51}$Cr-labeled EBV-transformed B cells from patient AVL3 were incubated for 30 min at 20° C. with the indicated concentrations of peptide. CTL 13 were then added at an effector:target ratio of 5:1, and chromium release was measured after 4 hr.

Example 5

Expression of the Gene Encoding Antigen AVL3-B

The expression of the gene (HERV-AVL3-B) encoding the AVL3-B antigen in normal tissues, tumor samples, and tumor cell lines was tested by reverse transcription-polymerase chain reaction (RT-PCR) amplification (Table 1). Expression of the gene encoding antigen AVL3-B was tested by RT-PCR amplification of total RNA with primers OPC646 and OPC600 as described above. A semi-quantitative measurement was obtained by combining a limiting number of PCR cycles and comparing the results with a standard curve of cDNA from AVL3-MEL cells. Samples were scored positive if their expression of the gene exceeded 3% of that found in AVL3-MEL cells. No expression was found in normal adult tissues except testis.

Among tumor samples, expression was found in approximately 50% of melanomas. Several melanoma cell lines also expressed the gene.

TABLE 1

Expression of the gene encoding antigen AVL3-B

| Normal tissues | | | positive samples |
|---|---|---|---|
| adrenals | – | Tumor cell lines | |
| bone marrow | – | colon carcinoma | 0/1 |
| brain | – | head and neck carcinomas | 0/3 |
| breast | – | lung carcinomas | 0/5 |
| colon | – | sarcomas | 1/2 |
| heart | – | bladder carcinoma | 0/1 |
| kidney | – | melanomas | 6/6 |
| liver | – | Tumor samples | |
| lung | – | colorectal carcinomas | 0/2 |
| muscle | – | breast carcinomas | 0/3 |
| ovary | – | sarcoma | 0/1 |
| prostate | – | prostatic carcinoma | 0/1 |
| retina | – | leukemias | 0/3 |
| skin | – | melanomas | 11/23 |
| testis | + | | |
| uterus | – | | |

Example 6

Identification of the Portion of Tumor Associated Genes Encoding Additional Tumor Rejection Antigens As discussed above, tumor associated polypeptides often are sources of more than one tumor rejection antigen peptides. This example describes the identification of additional TRAs encoded by HERV-AVL3-B. In a first method, available CTL clones directed against antigens presented by autologous tumor cells shown to express one or more of the tumor associated genes are screened for specificity against COS cells transfected with HERV-AVL3-B genes and autologous HLA alleles as described by Brichard et al. (*Eur. J. Immunol.* 26:224–230, 1996). CTL recognition of HERV-AVL3-B is determined by measuring release of TNF from the cytolytic T lymphocyte or by $^{51}$Cr release assay (Herin et al., *Int. J. Cancer* 39:390–396, 1987). If a CTL clone specifically recognizes a transfected COS cell, shorter fragments of the coding sequences are prepared and tested by transfecting COS cells to identify the region of the gene that encodes the peptide recognized by the CTL. Fragments of HERV-AVL3-B are prepared by exonuclease III digestion or other standard molecular biology methods such as PCR. Synthetic peptides are prepared and tested to confirm the exact sequence of the antigen.

Alternatively, CTL clones are generated by stimulating the peripheral blood lymphocytes (PBLs) of a patient with autologous normal cells transfected with DNA clones encoding HERV-AVL3-B polypeptides (e.g. SEQ ID NO:8) or with irradiated PBLs loaded with synthetic peptides corresponding to the putative proteins and matching the consensus for the appropriate HLA class I molecule to localize the antigenic peptide within the HERV-AVL3-B clones (see, e.g., van der Bruggen et al., *Eur. J. Immunol.* 24:3038–3043, 1994; Herman et al., *Immunogenetics* 43:377–383, 1996). Localization of one or more antigenic peptides in a protein sequence can be aided by HLA peptide binding predictions made according to established rules for binding potential (e.g., Parker et al, *J. Immunol.* 152:163, 1994; Rammensee et al., *Immunogenetics* 41:178–228, 1995). HLA binding predictions can conveniently be made using an algorithm available via the Internet on the National Institutes of Health World Wide Web site at URL http://bimas.dcrt.nih.gov.

Alternatively, CTL clones obtained by stimulation of lymphocytes with autologous tumor cells which express HERV-AVL3-B are screened for specificity against COS cells transfected with HERV-AVL3-B cDNA and autologous HLA alleles as described by Brichard et al. (*Eur. J. Immunol.* 26:224–230, 1996).

Optionally, shorter fragments of HERV-AVL3-B cDNAs are generated by PCR. Shorter fragments are used to provoke TNF release or $^{51}$Cr release as above.

Example 7

Identification of Tumor Associated Gene Encoded Tumor Rejection Antigen Peptides Synthetic peptides corresponding to portions of the shortest fragment of HERV-AVL3-B which provokes TNF release are prepared. Progressively shorter peptides are synthesized to determine the optimal HERV-AVL3-B tumor rejection antigen peptides for a given HLA molecule.

Synthetic peptides are tested for lysis of HLA expressing cells according to known procedures. For example, if the HLA which presents a peptide of interest is determined to be HLA-A2, then T2 cells can be used. T2 cells are HLA-A2+ cells which have an antigen-processing defect resulting in an increased capacity to present exogenous peptides. T2 cells are mixed with a synthetic peptide corresponding to the CTL-reactive portion of HERV-AVL3-B. CTL cells are added and lysis is measured after 4 hours to determine which peptides efficiently stimulate the lysis of T2 cells bearing HLA-A2. Other HLA expressing cells are known in the art or can be prepared by transfection with specific HLA clones.

To determine the optimal size of the synthetic peptide, peptides of decreasing size are synthesized based on the sequence of the peptide determined above, by successively removing one amino acid from the amino terminal end or the carboxy terminal end of the peptide. These peptides are tested for the ability to induce cell lysis of appropriate HLA expressing cells by CTL cells in a dose response assay. Lyophilized peptides are dissolved at 20 mg/ml in DMSO, then diluted to 2 mg/ml in 10 mM acetic acid and stored at −80° C. Target cells, e.g. HLA-A2+ T2 cells, are labeled with $^{51}$Cr, as described above, for 1 hour at 37° C. followed by extensive washing to remove unincorporated label. To confirm the necessity of the interaction of the peptide with the HLA, T2 cells optionally can be pretreated with an anti-HLA-A2 antibody, such as MA2.1 (Wölfel et al., *Eur. J. Immunol.* 24: 759–764, 1994), and then are incubated in 96-well microplates in the presence of various concentrations of peptides for 30 minutes at 37° C. CTLs which recognize the peptide presented by the HLA are then added in an equal volume of medium at an effector:target ratio of 30:1. Chromium-51 release is measured after 4 hours.

Example 8

Normal Cells are not Lysed by CTLs Which Lyse Cells Expressing Tumor Associated Genes This example describes CTL lysis experiments with various cell lines with or without incubation with the tumor associated gene derived peptides determined above. Tumor cells which express HERV-AVL3-B nucleic acids, normal B cells transformed with EBV (B-EBV) from the patient who is the source of the tumor cells, and normal peripheral blood lymphocytes from the same patient (PBL) are tested for lysis by CTL cells in a dose response assay. These cells are incubated with CTLs at the effector/target ratios determined to be optimal in the dose response assays detailed above, and assayed for lysis as described above. Lysis of only the HERV-AVL3-B-expressing tumor cells by the CTLs, demonstrates that B-EBV and PBL cells of the patient are not recognized by the CTLs because such cells do not normally express the tumor rejection antigen derived from HERV-AVL3-B proteins.

It is next determined whether these cells would be lysed by CTL if pulsed with a peptide derived from HERV-AVL3-B. The peptides selected on the basis of the experiments above are tested for the ability to induce cell lysis of HERV-AVL3-B-expressing tumor cells, B-EBV cells, and non-autologous cells which express the appropriate HLA by CTL cells in a dose response assay as in previous examples. B-EBV and PBL pulsed with preferred peptides are now lysed by CTLs, as are HERV-AVL3-B-expressing tumor cells and the non-autologous cells pulsed with preferred peptides.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference.

We claim:

1. An isolated nucleic acid molecule selected from the group consisting of:
    (a) nucleic acid molecules which fully hybridize under stringent conditions to a nucleic acid molecule having a nucleotide sequence set forth as SEQ ID NO:8, wherein the hybridizing nucleic acid molecule comprises a nucleotide sequence that encodes the amino acid sequence consisting of SEQ ID NO:9, and which code for a gene product that provokes a cytotoxic T cell immune response against a melanoma cancer cell that expresses the nucleic acid molecule,
    (b) nucleic acid molecules that differ from the nucleic acid molecules of (a) in codon sequence due to the degeneracy of the genetic code, and
    (c) complete complements of (a) and (b),
    wherein the stringent conditions are hybridization at 65° C. in hybridization buffer (3.5×SSC, 0.02% Ficoll, 0.02% polyvinyl pyrrolidone, 0.02% Bovine Serum Albumin, 25 mM $NaH_2PO_4$ (pH 7), 0.5% SDS, 2 mM EDTA); wherein SSC is 0.15M sodium chloride/ 0.015M sodium citrate. pH 7: SDS is sodium dodecyl sulphate; and EDTA is ethylenediaminetetracetic acid.

2. The isolated nucleic acid molecule of claim 1, wherein the isolated nucleic acid molecule comprises the nucleic acid sequence set forth as SEQ ID NO:8.

3. An isolated nucleic acid molecule selected from the group consisting of:
    (a) a fragment of SEQ ID NO:8 that encodes SEQ ID NO:9, and
    (b) complete complements of (a).

4. An expression vector comprising the isolated nucleic acid molecule of claim 1 operably linked to a promoter.

5. An isolated host cell transformed or transfected with the expression vector of claim 4.

6. A kit for detecting the presence of the expression of a tumor associated polypeptide precursor comprising SEQ ID NO:9, comprising at least one isolated first nucleic acid molecule consisting of a nucleotide sequence selected from the group consisting of SEQ ID NO:2 and SEQ ID NO:7, and at least one isolated second nucleic acid molecule consisting of a nucleotide sequence selected from the group consisting of SEQ ID NO:3, SEQ ID NO:4, SEQ ID NO:5, and SEQ ID NO:6, wherein the at least one first and the at least one second isolated nucleic acid molecules are constructed and arranged to selectively amplify at least a portion of an isolated nucleic acid molecule comprising SEQ ID NO:8.

7. An isolated nucleic acid molecule consisting of the nucleotide sequence set forth as SEQ ID NO:8 or a fragment thereof that encodes the amino acid sequence set forth as SEQ ID NO:9.

8. A method for producing a nucleic acid molecule set forth as SEQ ID NO:8 or polypeptide comprising SEQ ID NO:9, comprising providing a nucleic acid molecule consisting of the nucleotide sequence set forth as SEQ ID NO:8 or a fragment thereof that encodes the amino acid sequence of SEQ ID NO:9 operably linked to a promoter, expressing the nucleic acid molecule in an expression system, and isolating the expressed nucleic acid molecule or polypeptide from the expression system.

9. A method for making a nucleic acid molecule of claim 1 or a polypeptide comprising SEQ ID NO:9 comprising culturing an isolated host cell transformed or transfected with an expression vector comprising the isolated nucleic acid molecule of claim 1 operably linked to a promoter, and isolating the nucleic acid molecule or polypeptide from the isolated host cell.

10. An expression vector comprising the isolated nucleic acid molecule of claim 2 operably linked to a promoter.

11. An isolated host cell transformed or transfected with the expression vector of claim 10.

12. An expression vector comprising the isolated nucleic acid molecule of claim 7 operably linked to a promoter.

13. An isolated host cell transformed or transfected with the expression vector of claim 12.

14. The isolated nucleic acid molecule of claim 7, wherein the nucleic acid sequence which encodes the amino acid sequence set forth as SEQ ID NO:9 consists of SEQ ID NO:8 or a fragment of SEQ ID NO:8.

15. The isolated nucleic acid molecule of claim 14, wherein the fragment of SEQ ID NO:8 consists of nucleotides 413–819 of SEQ ID NO:8.

16. An expression vector comprising the isolated nucleic acid molecule of claim 14 operably linked to a promoter.

17. An isolated host cell transformed or transfected with the expression vector of claim 16.

18. An isolated nucleic acid molecule consisting of:

(a) a nucleotide sequence selected from the group consisting of SEQ ID NO:2, SEQ ID NO:3, SEQ ID NO:4, SEQ ID NO:5, SEQ ID NO:6 and SEQ ID NO:7, and (b) complete complements of (a).

* * * * *

SEQUENCE LISTING

```
<160> NUMBER OF SEQ ID NOS: 43

<210> SEQ ID NO 1
<211> LENGTH: 43
<212> TYPE: DNA
<213> ORGANISM: Artificial sequence
<220> FEATURE:
<221> NAME/KEY: primer_bind
<222> LOCATION: 1..43
<223> OTHER INFORMATION: synthetic oligo(dT) primer
<220> FEATURE:
<221> NAME/KEY: unsure
<222> LOCATION: 43..43
<223> OTHER INFORMATION: n = a, c, g or t

<400> SEQUENCE: 1
ataagaatgc ggccgctaaa ctattttttt tttttttttt tvn              43

<210> SEQ ID NO 2
<211> LENGTH: 18
<212> TYPE: DNA
<213> ORGANISM: Homo sapiens

<400> SEQUENCE: 2
gtaccagctg ctagcaag                                          18

<210> SEQ ID NO 3
<211> LENGTH: 18
<212> TYPE: DNA
<213> ORGANISM: Homo sapiens
```

-continued

```
<400> SEQUENCE: 3
tcgtcggtct tcattcca                                                      18

<210> SEQ ID NO 4
<211> LENGTH: 18
<212> TYPE: DNA
<213> ORGANISM: Homo sapiens

<400> SEQUENCE: 4
ggatcaaact gcaaggca                                                      18

<210> SEQ ID NO 5
<211> LENGTH: 18
<212> TYPE: DNA
<213> ORGANISM: Homo sapiens

<400> SEQUENCE: 5
cttccacata gactcctg                                                      18

<210> SEQ ID NO 6
<211> LENGTH: 18
<212> TYPE: DNA
<213> ORGANISM: Homo sapiens

<400> SEQUENCE: 6
agtgctactg aggacacc                                                      18

<210> SEQ ID NO 7
<211> LENGTH: 20
<212> TYPE: DNA
<213> ORGANISM: Homo sapiens

<400> SEQUENCE: 7
tgcagaggat ataaggagat                                                    20

<210> SEQ ID NO 8
<211> LENGTH: 2578
<212> TYPE: DNA
<213> ORGANISM: Homo sapiens

<400> SEQUENCE: 8
ctaatgaata caaagggctg tataagctca gggcccttgt tccctagaag caaggagccc        60
cctgacccct tctttaaaac agatcttttt gtctttgtct tcatttctgc gtttgtcctt       120
cttcttcagt cctgaactga cagccacaag tggcacctga acagggactt gaacaaagaa       180
ggtctgctgg agcagaaaaa gtgaaactga ccagatgaat gagaaaccct gggatgagtc       240
tgcctgcaga ggatataagg agatggataa accgtgtgag tgccctcaag ttgtgtgcga       300
ccatggaatg ggagactgga gggatacatg gatcccaact acaggcccag ctcctccagt       360
atgagccatg agccagttga atctgaatgt gaagatggaa tgaagaccga cgagagtcac       420
actgacgtca accctcataa catggggtca gatcaagaaa accacaccag aagctgagaa       480
actggtgtag tgccagggtc aggcaaaaac ccctgactcc atgtttatgg ccatgctagc       540
tgtaatatcc tgtgcagtat gattttctg tgcagaagca aaaacatatt gggcatattt        600
tcctaaccca ccggtagtgt gatcatactc tgaagcagca ctcctcctga gatatatcat       660
gatcaaggag catcagtacc aggacctcta actccccctg acacagagca attagactct       720
cataacaatg gtatcaatta taccactcca ttggagggac ttcctttatg tgtcacccag       780
```

-continued

```
gatacattgc tcaactgcag ttgccttgca gtttgatccc aagcatggtt gagttaccat      840
aaaaaaatta tgtacctatt agaccttagc tttattaata ttacttgtgt agttactaat      900
cactcctggc cccatcaccc aaattgtact gattatacag aatgggctcc ctttgataat      960
tctcaccccc ctccttgggc ccactgtctt ggccccttag ctagacaata gtccatgtta     1020
atgggagaca ttattgactg ggtccctgt ggtcattaag atgggagaga tgagaatcag      1080
accacatggc ataaacttca ctggcactgg tggcgaaact ttaacatctc ttcacttcaa     1140
cacactggga ttcaatccca atctgccatg caacttgctt ggcatggaac gggctttagc     1200
ccacctttgc ctcaatggca ttatcaagga agagaggtc caattcagga gtctatgtgg      1260
aaggcagcac tcccatatat gaatggcagc atttgggttg gacactatc caataatagt      1320 aatagtgctc aatacagttt aatgttacct ttgtaaaaaa tgtttgaaat ttgtgttttt     1380
aatccctatg ttttctagc agcaaaaaag gaccaactcc aggtaaacaa tgcccaattg      1440
aattgtgatt cctgtcaact ctatcattgc cttaatcata gcacaataca acacacagc      1500 atatccaccc taataattct aggtcgcatt cctggattat ggattcctgt aaatctatct     1560
gagccttggg cagccacccc cactttacat tttgtaaaac ttcttactca gcttactcat     1620
ggcactcgta gagccttagg catgataatt tttactatag tctccttaat tacattaata     1680
ccctctgttg tggtgtcctc agtagcactg gacagctcca ctcaaacagc tcaatatgca     1740
gaaaattgga tgcatacagc tgaccaggca tggatgtttc aaaataaaac taacactgag     1800
atacaaacag aagtggcaat gttaaagact actgttctgt ggctagaaga acaagtacaa     1860
agcttgcagt tgcagtagca attgcgttgt cattttaacc atactcatat ttgtgtaacc     1920
aattaggaat ataatcaaag tgaatatcca tggaaccttg taaaggccca tttacaggga     1980
gctgttacat ccaatgttac ttttgatatt aatgatttac aaagtaaaat tctaacagca     2040
cctcaatatc ttttttcataa ttattggaat aatgttacta tgtttctgtt ttttgttcat    2100
agtctgtaaa atcaactgga acaccaacca gcaattgaga gctgaacagc ctgcaattac     2160
ctttattcaa ttaaatcaaa agcagaaagg gggagatgtt ggaggctgaa agaatgaggg     2220
tcatgaccaa ctcagtatac cactggaggc tatgtgagca acagcaaac tgttctcatg      2280 aatacaggat attggcaagc tgacagctgc atctgccacc agaaggaatg ctgaggacag     2340
tcatgcatca ggcacagtgt tccttgtagt tatctatagg aacatctgga ccctgttgta     2400
taaagaaagc aattatttga gcctgtgata aatcaagcag ctgactaaaa ctgttacctc     2460
ttcctccctg ttgattctac ctaatacatg tgaagggctg tataagctca gggcccttgt     2520
tccctagaag caaggagccc cctgaccccct tctttacaac aaaaaaaaaa aaaaaaa       2578
```

<210> SEQ ID NO 9
<211> LENGTH: 9
<212> TYPE: PRT
<213> ORGANISM: Homo sapiens

<400> SEQUENCE: 9

Met Leu Ala Val Ile Ser Cys Ala Val
1               5

<210> SEQ ID NO 10
<211> LENGTH: 9
<212> TYPE: PRT
<213> ORGANISM: Homo sapiens

<400> SEQUENCE: 10

```
Glu Ala Asp Pro Thr Gly His Ser Tyr
1               5

<210> SEQ ID NO 11
<211> LENGTH: 9
<212> TYPE: PRT
<213> ORGANISM: Homo sapiens

<400> SEQUENCE: 11

Ser Ala Tyr Gly Glu Pro Arg Lys Leu
1               5

<210> SEQ ID NO 12
<211> LENGTH: 9
<212> TYPE: PRT
<213> ORGANISM: Homo sapiens

<400> SEQUENCE: 12

Glu Val Asp Pro Ile Gly His Leu Tyr
1               5

<210> SEQ ID NO 13
<211> LENGTH: 9
<212> TYPE: PRT
<213> ORGANISM: Homo sapiens

<400> SEQUENCE: 13

Phe Leu Trp Gly Pro Arg Ala Leu Val
1               5

<210> SEQ ID NO 14
<211> LENGTH: 10
<212> TYPE: PRT
<213> ORGANISM: Homo sapiens

<400> SEQUENCE: 14

Met Glu Val Asp Pro Ile Gly His Leu Tyr
1               5                   10

<210> SEQ ID NO 15
<211> LENGTH: 9
<212> TYPE: PRT
<213> ORGANISM: Homo sapiens

<400> SEQUENCE: 15

Ala Ala Arg Ala Val Phe Leu Ala Leu
1               5

<210> SEQ ID NO 16
<211> LENGTH: 8
<212> TYPE: PRT
<213> ORGANISM: Homo sapiens

<400> SEQUENCE: 16

Tyr Arg Pro Arg Pro Arg Arg Tyr
1               5

<210> SEQ ID NO 17
<211> LENGTH: 10
<212> TYPE: PRT
<213> ORGANISM: Homo sapiens

<400> SEQUENCE: 17

Ser Pro Ser Ser Asn Arg Ile Arg Asn Thr
1               5                   10
```

<210> SEQ ID NO 18
<211> LENGTH: 9
<212> TYPE: PRT
<213> ORGANISM: Homo sapiens

<400> SEQUENCE: 18

Val Leu Pro Asp Val Phe Ile Arg Cys
1               5

<210> SEQ ID NO 19
<211> LENGTH: 10
<212> TYPE: PRT
<213> ORGANISM: Homo sapiens

<400> SEQUENCE: 19

Val Leu Pro Asp Val Phe Ile Arg Cys Val
1               5                   10

<210> SEQ ID NO 20
<211> LENGTH: 9
<212> TYPE: PRT
<213> ORGANISM: Homo sapiens

<400> SEQUENCE: 20

Glu Glu Lys Leu Ile Val Val Leu Phe
1               5

<210> SEQ ID NO 21
<211> LENGTH: 9
<212> TYPE: PRT
<213> ORGANISM: Homo sapiens

<400> SEQUENCE: 21

Glu Glu Lys Leu Ser Val Val Leu Phe
1               5

<210> SEQ ID NO 22
<211> LENGTH: 10
<212> TYPE: PRT
<213> ORGANISM: Homo sapiens

<400> SEQUENCE: 22

Ala Cys Asp Pro His Ser Gly His Phe Val
1               5                   10

<210> SEQ ID NO 23
<211> LENGTH: 10
<212> TYPE: PRT
<213> ORGANISM: Homo sapiens

<400> SEQUENCE: 23

Ala Arg Asp Pro His Ser Gly His Phe Val
1               5                   10

<210> SEQ ID NO 24
<211> LENGTH: 9
<212> TYPE: PRT
<213> ORGANISM: Homo sapiens

<400> SEQUENCE: 24

Ser Tyr Leu Asp Ser Gly Ile His Phe
1               5

```
<210> SEQ ID NO 25
<211> LENGTH: 9
<212> TYPE: PRT
<213> ORGANISM: Homo sapiens

<400> SEQUENCE: 25

Ser Tyr Leu Asp Ser Gly Ile His Ser
1               5

<210> SEQ ID NO 26
<211> LENGTH: 9
<212> TYPE: PRT
<213> ORGANISM: Homo sapiens

<400> SEQUENCE: 26

Met Leu Leu Ala Val Leu Tyr Cys Leu
1               5

<210> SEQ ID NO 27
<211> LENGTH: 9
<212> TYPE: PRT
<213> ORGANISM: Homo sapiens

<400> SEQUENCE: 27

Tyr Met Asn Gly Thr Met Ser Gln Val
1               5

<210> SEQ ID NO 28
<211> LENGTH: 9
<212> TYPE: PRT
<213> ORGANISM: Homo sapiens

<400> SEQUENCE: 28

Ala Phe Leu Pro Trp His Arg Leu Phe
1               5

<210> SEQ ID NO 29
<211> LENGTH: 9
<212> TYPE: PRT
<213> ORGANISM: Homo sapiens

<400> SEQUENCE: 29

Ser Glu Ile Trp Arg Asp Ile Asp Phe
1               5

<210> SEQ ID NO 30
<211> LENGTH: 9
<212> TYPE: PRT
<213> ORGANISM: Homo sapiens

<400> SEQUENCE: 30

Tyr Glu Ile Trp Arg Asp Ile Asp Phe
1               5

<210> SEQ ID NO 31
<211> LENGTH: 15
<212> TYPE: PRT
<213> ORGANISM: Homo sapiens

<400> SEQUENCE: 31

Gln Asn Ile Leu Leu Ser Asn Ala Pro Leu Gly Pro Gln Phe Pro
1               5                   10                  15

<210> SEQ ID NO 32
<211> LENGTH: 15
```

```
<212> TYPE: PRT
<213> ORGANISM: Homo sapiens

<400> SEQUENCE: 32

Asp Tyr Ser Tyr Leu Gln Asp Ser Asp Pro Asp Ser Phe Gln Asp
1               5                   10                  15

<210> SEQ ID NO 33
<211> LENGTH: 10
<212> TYPE: PRT
<213> ORGANISM: Homo sapiens

<400> SEQUENCE: 33

Glu Ala Ala Gly Ile Gly Ile Leu Thr Val
1               5                   10

<210> SEQ ID NO 34
<211> LENGTH: 9
<212> TYPE: PRT
<213> ORGANISM: Homo sapiens

<400> SEQUENCE: 34

Ala Ala Gly Ile Gly Ile Leu Thr Val
1               5

<210> SEQ ID NO 35
<211> LENGTH: 9
<212> TYPE: PRT
<213> ORGANISM: Homo sapiens

<400> SEQUENCE: 35

Ile Leu Thr Val Ile Leu Gly Val Leu
1               5

<210> SEQ ID NO 36
<211> LENGTH: 9
<212> TYPE: PRT
<213> ORGANISM: Homo sapiens

<400> SEQUENCE: 36

Lys Thr Trp Gly Gln Tyr Trp Gln Val
1               5

<210> SEQ ID NO 37
<211> LENGTH: 9
<212> TYPE: PRT
<213> ORGANISM: Homo sapiens

<400> SEQUENCE: 37

Ile Thr Asp Gln Val Pro Phe Ser Val
1               5

<210> SEQ ID NO 38
<211> LENGTH: 9
<212> TYPE: PRT
<213> ORGANISM: Homo sapiens

<400> SEQUENCE: 38

Tyr Leu Glu Pro Gly Pro Val Thr Ala
1               5

<210> SEQ ID NO 39
<211> LENGTH: 10
<212> TYPE: PRT
<213> ORGANISM: Homo sapiens
```

-continued

```
<400> SEQUENCE: 39

Leu Leu Asp Gly Thr Ala Thr Leu Arg Leu
1               5                   10

<210> SEQ ID NO 40
<211> LENGTH: 10
<212> TYPE: PRT
<213> ORGANISM: Homo sapiens

<400> SEQUENCE: 40

Val Leu Tyr Arg Tyr Gly Ser Phe Ser Val
1               5                   10

<210> SEQ ID NO 41
<211> LENGTH: 9
<212> TYPE: PRT
<213> ORGANISM: Homo sapiens

<400> SEQUENCE: 41

Leu Tyr Val Asp Ser Leu Phe Phe Leu
1               5

<210> SEQ ID NO 42
<211> LENGTH: 12
<212> TYPE: PRT
<213> ORGANISM: Homo sapiens

<400> SEQUENCE: 42

Lys Ile Ser Gly Gly Pro Arg Ile Ser Tyr Pro Leu
1               5                   10

<210> SEQ ID NO 43
<211> LENGTH: 9
<212> TYPE: PRT
<213> ORGANISM: Homo sapiens

<400> SEQUENCE: 43

Tyr Met Asp Gly Thr Met Ser Gln Val
1               5
```